United States Patent
Gatto-Menking et al.

(10) Patent No.: US 7,141,436 B2
(45) Date of Patent: Nov. 28, 2006

(54) IMMUNOASSAY AND REAGENTS AND KITS FOR PERFORMING THE SAME

(75) Inventors: Deborah L. Gatto-Menking, Bel Air, MD (US); Michael T. Goode, Baltimore, MD (US)

(73) Assignee: Science and Technology Corp., Hampton, VA (US)

( * ) Notice: Subject to any disclaimer, the term of this patent is extended or adjusted under 35 U.S.C. 154(b) by 476 days.

(21) Appl. No.: 10/147,965

(22) Filed: May 20, 2002

(65) Prior Publication Data

US 2003/0108973 A1 Jun. 12, 2003

Related U.S. Application Data

(63) Continuation of application No. 09/433,787, filed on Nov. 3, 1999, now abandoned.

(51) Int. Cl.
G01N 33/543 (2006.01)
(52) U.S. Cl. ............ 436/518; 436/526; 436/535; 436/172; 435/7.1; 435/7.2; 435/7.92; 435/7.93; 435/7.94; 435/7.95; 435/975; 53/289; 426/392
(58) Field of Classification Search ............ 436/518, 436/526, 535, 172; 435/7.1, 7.2, 7.92–7.95, 435/975; 53/289; 426/392
See application file for complete search history.

(56) References Cited

U.S. PATENT DOCUMENTS

| | | | |
|---|---|---|---|
| 4,444,879 A * | 4/1984 | Foster et al. | 435/7.95 |
| 4,468,469 A | 8/1984 | Atkinson et al. | |
| 4,622,293 A | 11/1986 | Ellis et al. | |
| 4,818,686 A | 4/1989 | Kortright et al. | |
| 4,931,385 A | 6/1990 | Block et al. | |
| 5,017,559 A | 5/1991 | Dosako et al. | |
| 5,061,445 A | 10/1991 | Zoski et al. | |
| 5,068,088 A | 11/1991 | Hall et al. | |
| 5,093,268 A | 3/1992 | Leventis et al. | |
| 5,102,788 A | 4/1992 | Cole | |
| 5,147,806 A | 9/1992 | Kamin et al. | |
| 5,189,549 A | 2/1993 | Leventis et al. | |
| 5,202,267 A | 4/1993 | Ditlow et al. | |
| 5,221,605 A | 6/1993 | Bard et al. | |
| 5,238,808 A | 8/1993 | Bard et al. | |
| 5,247,243 A | 9/1993 | Hall et al. | |
| 5,296,191 A | 3/1994 | Hall et al. | |

(Continued)

FOREIGN PATENT DOCUMENTS

DE 3428953 A1 * 2/1986

OTHER PUBLICATIONS

Blackburn, et al., *Clinical Chemistry*, vol. 37, No. 9, pp. 1534-1539 (1991).

(Continued)

*Primary Examiner*—Long V. Le
*Assistant Examiner*—Pensee T. Do
(74) *Attorney, Agent, or Firm*—Oblon, Spivak, McClelland, Maier & Neustadt, P.C.

(57) ABSTRACT

A sandwich immunoassay is disclosed that provides simple to perform yet sensitive identification of analytes in samples. All assay constituents needed (except analyte to be detected) for one assay are dried. Upon reconstitution with sample, a 10 to 15 minute incubation gives a rapid and convenient detection assay capability. The method incorporates the capture of antigen to an immobilized capture antibody. A labeled reporter antibody with the molecule, binds to the antigen to form an immunocomplex capable of generating a detectable signal.

58 Claims, 12 Drawing Sheets

U.S. PATENT DOCUMENTS

| | | | |
|---|---|---|---|
| 5,310,687 A | 5/1994 | Bard et al. | |
| 5,384,265 A * | 1/1995 | Kidwell et al. | 436/525 |
| 5,399,500 A | 3/1995 | Oppenheimer et al. | |
| 5,453,356 A | 9/1995 | Bard et al. | |
| 5,466,416 A | 11/1995 | Ghaed et al. | |
| 5,543,112 A | 8/1996 | Ghead et al. | |
| 5,591,581 A | 1/1997 | Massey et al. | |
| 5,597,910 A | 1/1997 | Gudibande et al. | |
| 5,610,075 A | 3/1997 | Stahl-Rees | |
| 5,624,637 A | 4/1997 | Ghaed et al. | |
| 5,632,956 A | 5/1997 | Ghaed et al. | |
| 5,641,623 A | 6/1997 | Martin | |
| 5,643,713 A | 7/1997 | Liang et al. | |
| 5,656,503 A * | 8/1997 | May et al. | 436/514 |
| 5,679,519 A | 10/1997 | Oprandy | |
| 5,686,244 A | 11/1997 | Gudibande et al. | |
| 5,700,427 A | 12/1997 | Ghaed et al. | |
| 5,705,402 A * | 1/1998 | Leland et al. | 436/526 |
| 5,714,089 A | 2/1998 | Bard et al. | |
| 5,716,781 A | 2/1998 | Massey et al. | |
| 5,720,922 A | 2/1998 | Ghaed et al. | |
| 5,731,147 A | 3/1998 | Bard et al. | |
| 5,744,367 A | 4/1998 | Talley et al. | |
| 5,746,974 A | 5/1998 | Massey et al. | |
| 5,770,459 A * | 6/1998 | Massey et al. | 436/526 |
| 5,779,976 A | 7/1998 | Leland et al. | |
| 5,798,083 A | 8/1998 | Massey et al. | |
| 5,804,400 A | 9/1998 | Martin et al. | |
| 5,807,752 A | 9/1998 | Brizgys et al. | |
| 5,811,236 A | 9/1998 | Massey et al. | |
| 5,846,485 A | 12/1998 | Leland et al. | |
| 5,858,676 A | 1/1999 | Yang et al. | |
| 5,935,779 A | 8/1999 | Massey et al. | |
| 5,945,344 A | 8/1999 | Hayes et al. | |
| 5,962,218 A | 10/1999 | Leland et al. | |
| 6,159,686 A * | 12/2000 | Kardos et al. | 435/6 |
| 6,649,420 B1 * | 11/2003 | Cantor | 436/540 |
| 6,696,304 B1 * | 2/2004 | Davies | 436/518 |

OTHER PUBLICATIONS

Gatto-Menking, et al., *Biosensors & Bioelectronics*, vol. 10, pp. 501-507 (1995).

Mitrunen, et al., *Clinical Chemistry*, vol. 41, No. 8, pp. 1115-1120 (1995).

Merioe, et al., *Clinical Chemistry*, vol. 42., No. 9, pp. 1513-1517 (1996).

Loevgren, et al., *Clinical Chemistry*, vol. 42, No. 8, pp. 1196-1201 (1996).

Gatto-Menking, et al., Science and Technology Corp., Technical Report 3139, pp. 36-43 (1997).

Gatto-Menking, et al., Science and Technology Corp., Technical Report 2908, pp. 14-25 (1995).

* cited by examiner

BLOCKING FORMAT A

BLOCKING FORMAT B

IMMUNOASSAY AND REAGENTS AND KITS FOR PERFORMING THE SAME

CROSS-REFERENCE TO RELATED APPLICATIONS

The present application is a continuation of U.S. application Ser. No. 09/443,787, filed on Nov. 3, 1999 now abandoned.

STATEMENT REGARDING FEDERALLY FUNDED PROJECT

The United States Government owns certain rights in the present invention pursuant to funding from the U.S. Army, Contract No. DAAM01-97-D-0007.

BACKGROUND OF THE INVENTION

1. Field of Invention

The present invention relates to novel immunoassay methods and devices or kits that utilize a sandwich assay for detection of an antigen or hapten in a sample, particularly a biological sample. In a preferred embodiment, the present invention relates to a simple one-step electrochemiluminescent (ECL) assay approach that requires approximately 15 minutes for identification and/or quantification of an antigen or analyte. The present invention also relates to reagents and kits useful for carrying our such immunoassays.

2. Discussion of the Background

In the medical, environmental, and food safety communities, immunodiagnostic testing has become the means to provide simplistic assessment and rapid identification of diseases and contaminants that are harmful to society. To prevent the occurrence of protracted illness and/or endemic disease, there is a need for simplistic confirmatory assays that provide qualitative and semi-quantitative assessment for the detection of antigen in a clinical specimen, soil or water sample, or food. In addition, in recent years due to the realization of the threat of national terrorism, many diagnostic tests are designed to be performed at satellite sites other than established laboratories. This scenario presents a critical need to provide very simple, reliable, and easy to use diagnostic assays that may be performed confidently by non-technical or lay personnel. Moreover, in this respect, most sophisticated bioassay platforms are useful as long as they do not require extensive operator manipulations that lead to the rapid and facile determination of the presence or absence of analyte in a clinical, environmental, or food sample.

Currently, immunoassay-based detection systems rely upon an antibody-antigen inter-action that requires the addition of multiple assay components in a sequential manner to produce a detectable event. Although reliable for positive identification, present assay procedures and reagent preparation are involved and time consuming. The major drawback associated with present procedures is the sequential addition and transfer of multiple reagents to produce an assay. Each additional step for a detection assay increases the degree of difficulty for execution by the operator and is prone to misuse, thereby, resulting in a higher margin for error.

Thus, there remains a need for immunoassays which overcome the above-mentioned drawbacks. There also remains a need for reagents and kits useful for carrying out such immunoassays.

SUMMARY OF THE INVENTION

Accordingly, it is one object of the present invention to provide novel immunoassays.

It is another object of the present invention to provide novel immunoassays which are convenient to carry out.

It is another object of the present invention to provide novel immunoassays which minimize the number of steps performed by the analyst.

It is another object of the present invention to provide novel immunoassays which exhibit an improved signal to noise ratio.

It is another object of the present invention to provide novel immunoassays which exhibit a decrease background signal.

It is another object of the present invention to provide novel reagents useful for carrying our such immunoassays.

It is another object of the present invention to provide novel kits useful for carrying our such immunoassays.

These and other objects, which will become apparent during the following detailed description, have been achieved by the inventors' discovery that an immunoassay method comprising the steps:

(i) incubating a liquid sample, which may contain an analyte, with a reagent mixture, wherein said reagent mixture comprises an immobilized capture antibody and a labeled reporter antibody and wherein said immobilized capture antibody and said labeled reporter antibody bind specifically to said analyte; and (ii) measuring a signal attributable to a complex (sandwich) formed by binding of said immobilized capture antibody and said labeled reporter antibody to said analyte, wherein said reagent mixture has been prepared by drying a liquid comprising said labeled reporter antibody in the presence of said immobilized capture antibody, overcome the above-described drawbacks.

The inventors have also discovered that reagents comprising:

(1) an immobilized capture antibody; and
(2) a labeled reporter antibody, wherein said immobilized capture antibody and said labeled reporter antibody bind specifically to a same analyte, and wherein said reagent mixture has been prepared by drying a liquid comprising said labeled reporter antibody in the presence of said immobilized capture antibody, are useful for carrying out such immunoassays.

The inventors have also discovered that kits, comprising:

(A) a container; and
(B) a reagent comprising:
(1) an immobilized capture antibody; and
(2) a labeled reporter antibody, wherein said immobilized capture antibody and said labeled reporter antibody bind specifically to a same analyte, and wherein said reagent mixture has been prepared by drying a liquid comprising said labeled reporter antibody in the presence of said immobilized capture antibody, and wherein said reagent is contained in said container, are useful for carrying out such immunoassays.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1A:
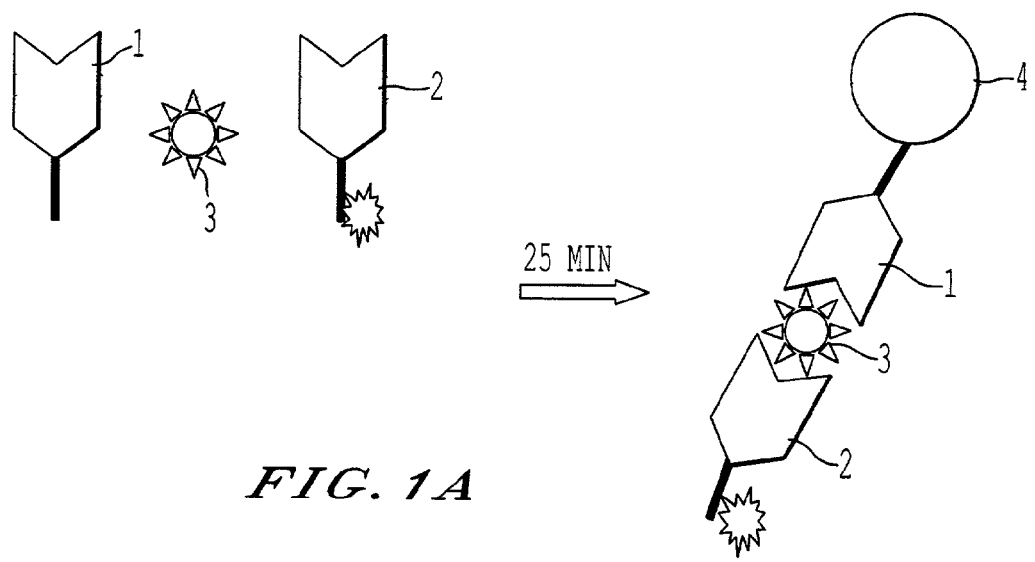
FIG. 1 is a schematic representation of a conventional ECL sandwich assay.

Thus, in a first embodiment, the present invention provides novel reagents which comprise:

(1) an immobilized capture antibody; and
(2) a labeled reporter antibody, wherein said immobilized capture antibody and said labeled reporter antibody bind specifically to a same analyte, and wherein said reagent mixture has been prepared by drying a liquid comprising said labeled reporter antibody in the presence of said immobilized capture antibody.

The capture antibody may be any which binds specifically to the analyte of interest. Preferably, the capture antibody is a monoclonal antibody. A large number of monoclonal antibodies which bind to various analytes of interest are available, see, e.g., *Biochemicals and Reagents for Life Science Research*, Sigma-Aldrich Co., P.O. Box 14508, St. Louis, Mo., 63178, 1999; the Life Technologies Catalog, Life Technologies, Gaithersburg, Md.; and the Pierce Catalog, Pierce Chemical Company, P.O. Box 117, Rockford, Ill. 61105, 1994, all of which are incorporated herein by reference. Examples of analytes to which the capture antibody binds specifically include bacterial toxins, viruses, bacteria, proteins, hormones, DNA, RNA, drugs, antibiotics, nerve toxins, etc.

Particularly preferred antibodies are monoclonal antibodies which bind specifically to β-actin, DNA, digoxin, insulin, progesterone, human leukocyte markers, human interleukin-10, human interferon, human fibrinogen, p53, hepatitis B virus or a portion thereof, HIV virus or a portion thereof, tumor necrosis factor, and FK-506.

The capture antibody is immobilized on a support. The support may take any convenient form. Preferred supports are membranes, beads, or even the walls of a container. The support may be composed of any material on which antibodies are conventionally immobilized, such as nitrocellulose, polystyrene, or polyvinyl chloride. More preferably, the support is a bead, particularly a polystyrene bead.

In some embodiments, a characteristic of the support is relied upon to generate or detect the signal attributable to the sandwich complex formed by the binding of the capture antibody and the reporter antibody to the analyte. For example, in an electrochemiluminescent (ECL) assay, it is preferred that the support be a paramagnetic bead. Such paramagnetic beads are disclosed in U.S. Pat. Nos. 5,962,218; 5,945,344; 5,935,779; 5,858,676; 5,846,485; 5,811,236; 5,804,400; 5,798,083; 5,779,976; 5,770,459; 5,746,974; 5,744,367; 5,731,147; 5,720,922; 5,716,781; 5,714,089; 5,705,402; 5,700,427; 5,686,244; 5,679,519; 5,643,713; 5,641,623; 5,632,956; 5,624,637; 5,610,075; 5,597,910; 5,591,581; 5,543,112; 5,466,416; 5,453,356; 5,310,687; 5,296,191; 5,247,243; 5,238,808; 5,221,605; 5,189,549; 5,147,806; 5,093,268; 5,068,088; and 5,061,445; in and Dong, L. et al, *Anal. Biochem.*, vol. 236, pp. 344–347 (1996); Blohm, et al, *Biomedical Products*, vol. 21, No. 4: 60 (1996); Jameison, F., et al, *Anal. Chem.*, vol. 68, pp. 1298–1302 (1996); Kibbey, M. et al, *Nature Biotechnology*, vol. 14, no. 3, pp. 259–260 (1996); Yu, H., et al, *Applied and Environmental Microbiology*, vol. 62, no. 2, pp. 587–592 (1996); Williams Richard, Ph.D., *American Biotechnology*, page 26 (January, 1996); Darsley, M., et al, *Biomedical Products*, vol. 21, no. 1, p. 133 (January, 1996); Kobrynski, L., et al, *Clinical and Diagnostic Laboratory Immunology*, vol. 3, no. 1, pp. 42–46 (January 1996); Williams, Richard, Ph.D. *IVD Technology*, pp.28–31 (November, 1995); Deaver, D. R., *Nature*, vol. 377, pp. 758–760 (Oct. 26, 1995); Yu, H., et al, *BioMedical Products*, vol. 20, no. 10, p. 20 (October, 1995); Kibbey, M., et al, *BioMedical Products*, vol. 20, no. 9, p. 116 (September, 1995); Schutzbank, T. E., et al, *Journal of Clinical Microbiology*, vol. 33, pp. 2036–2041 (August, 1995); Stem, H. J., et al, *Clinical Biochemistry*, vol. 28, pp. 470–472 (August, 1995); Carlowicz, M., *Clinical Laboratory News*, vol. 21, no. 8, pp. 1–2 (August 1995); Gatto-Menking, D. L., et al, *Biosensors & Bioelectronics*, vol. 10, pp. 501–507 (July, 1995); Yu, H., et al, *Journal of Bioluminescence and Chemiluminescence*, vol. 10, pp. 239–245 (1995); Van Gemen, B., et al, *Journal of Virology Methods*, vol. 49, pp. 157–168 (1994); Yang, H., et al, *Bio/Technology*, vol. 12, pp. 193–194 (1994); Kenten, J. H., et al, *Clinical Chemistry*, vol. 38, pp. 873–879 (1992); Kenten, J. H., "Electrochemiluminescence," in *Non-radioactive Labeling and Detection of Biomolecules*, Kessler, Ed., Springer, Berlin, pp. 175–179 (1992); Gudibande, S., et al, *Journal of Molecular and Cellular Probes*, vol. 6, pp. 495–503 (1992); Kenten, J. H., et al, *Clinical Chemistry*, vol. 37, pp. 1626–1632 (1991); Blackburn G. F., et al, *Clinical Chemistry*, vol. 37, pp. 1534–1539 (1991), all of which are incorporated herein by reference.

The capture antibody may be immobilized on the support in any conventional means, e.g., absorption, covalent binding with a crosslinking agent, or covalent linkage resulting from chemical activation of either or both of the support or the capture antibody. The immobilization of the capture antibody may be accomplished by immobilizing one half of a binding pair, e.g., streptavidin, to the support and binding the other half of the same binding pair, e.g., biotin, to the capture antibody. Suitable means for immobilizing the capture antibody on the support are disclosed in the Pierce Catalog, Pierce Chemical Company, P.O. Box 117, Rockford, Ill. 61105, 1994, which is incorporated herein by reference.

The reporter antibody binds specifically to the same analyte to which the capture antibody binds specifically. The reporter antibody is also preferably a monoclonal antibody. Preferably, the reporter antibody binds to a different epitope of the analyte than the capture antibody.

The reporter antibody is labeled with an atom, moiety, functional group, or molecule which is relied upon to generate or detect the signal attributable to the sandwich complex formed by the binding of the capture antibody and the reporter antibody to the analyte. For example, in a radiochemical assay, the reporter antibody may be labeled with a radioactive isotope of iodine. Alternatively, the reporter antibody may be labeled with an enzyme, horse radish peroxidase, which can be used in a colorimetric assay. The reporter antibody may also be labeled with a time-resolved fluorescence reporter. Such reporters are disclosed in Hemmila, I., et al, *J. Biochem. Biophys. Methods*, vol. 26, pp. 283–290 (1993); Kakabakos, S. E., et al, *Clin. Chem.*, vol. 38, pp. 338–342 (1992); Xu, Y.-Y., et al, *Clin. Chem.*, pp. 2038–2043 (1992); Hemmila, I., et al, *Scand. J. Clin. Lab. Invest.*, vol. 48, pp. 389–400 (1988); *Bioluminescence and Chemiluminescence Proceedings of the 9th International Symposium* 1996, J. W. Hastings et al, Eds., Wiley, N.Y., 1996; *Bioluminescence and Chemiluminescence Instruments and Applications*, Knox Van Dyre, Ed., CRC Press, Boca Raton, 1985; I. Hemmila, *Applications of Fluoresence in Immunoassays, Chemical Analysis*, Volume 117, Wiley, N.Y., 1991; and Balckburn, G. F., et al, *Clin. Chem.*, vol. 37, p. 1534 (1991), all of which are incorporated herein by reference.

In a preferred embodiment, the reporter antibody is labeled with a moiety, functional group, or molecule which is useful for generating a signal in an electrochemiluminescent (ECL) assay. Such moieties, functional groups, or molecules are disclosed in U.S. Pat. Nos. 5,962,218; 5,945,344; 5,935,779; 5,858,676; 5,846,485; 5,811,236; 5,804,400; 5,798,083; 5,779,976; 5,770,459; 5,746,974; 5,744,367; 5,731,147; 5,720,922; 5,716,781; 5,714,089; 5,705,402; 5,700,427; 5,686,244; 5,679,519; 5,643,713; 5,641,623; 5,632,956; 5,624,637; 5,610,075; 5,597,910; 5,591,581; 5,543,112; 5,466,416; 5,453,356; 5,310,687; 5,296,191; 5,247,243; 5,238,808; 5,221,605; 5,189,549; 5,147,806; 5,093,268; 5,068,088; and 5,061,445; in and Dong, L. et al, *Anal. Biochem.*, vol. 236, pp. 344–347 (1996); Blohm, et al, *Biomedical Products*, vol. 21, No. 4: 60 (1996); Jameison, F., et al, *Anal. Chem.*, vol. 68, pp. 1298–1302 (1996); Kibbey, M. et al, *Nature Biotechnology*, vol.14, no. 3, pp. 259–260 (1996); Yu, H., et al, *Applied and Environmental Microbiology*, vol. 62, no. 2, pp. 587–592 (1996); Williams Richard, Ph.D., *American Biotechnology*, page 26 (January, 1996); Darsley, M., et al, *Biomedical Products*, vol. 21, no. 1, p. 133 (January, 1996); Kobrynski, L., et al, *Clinical and Diagnostic Laboratory Immunology*, vol. 3, no. 1, pp. 42–46 (January 1996); Williams, Richard, Ph.D. *IVD Technology*, pp.28–31 (November, 1995); Deaver, D. R., *Nature*, vol. 377, pp. 758–760 (Oct. 26, 1995); Yu, H., et al, *BioMedical Products*, vol. 20, no. 10, p. 20 (October, 1995); Kibbey, M., et al, *BioMedical Products*, vol. 20, no. 9, p. 116 (September, 1995); Schutzbank, T. E., et al, *Journal of Clinical Microbiology*, vol. 33, pp. 2036–2041 (August, 1995); Stern, H. J., et al, *Clinical Biochemistry*, vol. 28, pp. 470–472 (August, 1995); Carlowicz, M., *Clinical Laboratory News*, vol. 21, no. 8, pp. 1–2 (August 1995); Gatto-Menking, D. L., et al, *Biosensors & Bioelectronics*, vol. 10, pp. 501–507 (July, 1995); Yu, H., et al, *Journal of Bioluminescence and Chemiluminescence*, vol. 10, pp. 239–245 (1995); Van Gemen, B., et al, *Journal of Virology Methods*, vol. 49, pp. 157–168 (1994); Yang, H., et al, *Bio/Technology*, vol. 12, pp. 193–194 (1994); Kenten, J. H., et al, *Clinical Chemistry*, vol. 38, pp. 873–879 (1992); Kenten, J. H., "Electrochemiluminescence," in *Non-radioactive Labeling and Detection of Biomolecules*, Kessler, Ed., Springer, Berlin, pp. 175–179 (1992); Gudibande, S., et al, *Journal of Molecular and Cellular Probes*, vol. 6, pp. 495–503 (1992); Kenten, J. H., et al, *Clinical Chemistry*, vol. 37, pp. 1626–1632 (1991); Blackburn G. F., et al, *Clinical Chemistry*, vol. 37, pp. 1534–1539 (1991), all of which are incorporated herein by reference. In a particularly preferred embodiment, the reporter antibody is labeled with ruthenium, more particularly ruthenium (II) tris bypyridal (Ru $(bpy)_3^{2+}$).

The reagents of the present invention are prepared by drying the labeled reporter antibody in the presence of the immobilized capture antibody. When the capture antibody is immobilized on the wall of a container or vessel, the reagent may be prepared by coating the wall of the container, which has immobilized capture antibody, with a liquid, preferably aqueous solution, which contains the labeled reporter antibody and then drying to obtain a reagent in which a layer of lyophilized labeled reporter antibody is formed on the wall of the container, which has immobilized capture antibody. When the capture antibody is immobilized on a bead, the reagent may be prepared by drying a liquid or liquids, preferably aqueous solution(s), which contains the immobilized capture antibody and the labeled reporter antibody, to obtain a reagent in which a dried solid which contains the immobilized capture antibody and the labeled reporter antibody. In a preferred embodiment, the dried solid is an intimate mixture of the immobilized capture antibody and the labeled reporter antibody.

Although the drying may be accomplished by simple air drying at room temperature and atmospheric pressure, it may be preferred to assist the drying by use of a decreased pressure or elevated temperature or a combination thereof. In a particularly preferred embodiment, the drying is accomplished by lyophilization or freeze drying. Methods and apparatus for lyophilizing materials, in particular biological materials, are well known to those skilled in the art.

For the specific embodiment described in the examples below, the reagent contains the labeled reporter antibody in equimolar or equiequivalent amounts. However, the exact ratio of the capture antibody to the reporter antibody can be varied depending on the relative binding specificities of the capture antibody and the reporter antibody, the type of signal relied upon and other variations of the assay conditions. Determination of the optimum ratio of the capture antibody to the reporter antibody for any given set of conditions is within the skill of the average artisan. The desired ratio of labeled reporter antibody to immobilized capture antibody may be achieved by simply adding these components to the system to be lyophilized in that desired ratio.

In some embodiments, the reagent of the present invention may further comprise a lyophilization buffer. Lyophilization buffers are well known in the art and typically contain phosphate buffer and optionally one or more cryoprotectants.

The reagent of the present invention may further comprise a compound such as trihalose or sucrose. In this embodiment, the trihalose or sucrose may exist as a layer between the immobilized capture antibody and the labeled reporter antibody. Such systems can be formed by sequential drying and/or lyophilization of first the trihalose or sucrose and then the labeled reporter antibody.

In a particularly preferred embodiment, the support is blocked to reduce or prevent the nonspecific binding of the labeled reporter antibody to the support. Any conventional blocking agents can be used. Suitable blocking agents are described in U.S. Pat. Nos. 5,807,752; 5,202,267; 5,399,500; 5,102,788; 4,931,385; 5,017,559; 4,818,686; 4,622,293; 4,468,469; and in CA 1,340,320; WO 97/05485; EP-A1-566,205; EP-A2-444,649; and EP-A1-165,669, all of which are incorporated herein by reference. Preferred blocking agents include goat serum, bovine serum albumin, and milk proteins ("blotto"). The support may be blocked by absorption of the blocking agent either prior to or after immobilization of the capture antibody. Preferably, the support is blocked by absorption of the blocking agent after immobilization of the capture antibody. The exact conditions for blocking the support, including the exact amount of blocking agent used, will depend on the identities of the blocking agent and support but may be easily determined using the assays and protocols described in the Examples below.

In another embodiment, the present invention provides kits, comprising:

(A) a container; and
(B) a reagent comprising:
(1) an immobilized capture antibody; and
(2) a labeled reporter antibody, wherein said immobilized capture antibody and said labeled reporter antibody bind specifically to a same analyte, and wherein said reagent mixture has been prepared by lyophilizing a liquid comprising said labeled reporter antibody in the presence of said immobilized capture antibody, and wherein said reagent is contained in said container.

The reagent and the components thereof in this embodiment are the same as discussed above. The container may be any which is useful for storing the reagent and/or for carrying out the immunoassay of the present invention. Thus, the container may be a bag or pouch. Preferably, the container is suitable for both storing the reagent and for carrying out the present immunoassay. Thus, the container is preferably a membrane, test tube or a microtitre plate. More preferably, the container is a test tube or a microtitre plate. Most preferably, the container is a test tube.

In another preferred embodiment, the container can be closed or sealed to protect the reagent from exposure to contamination by air or moisture. Alternatively, the container which contains the reagent may itself be sealed or enclosed in a second container to protect the reagent from exposure to contamination by air or moisture.

The kits of the present invention may further comprise written instructions in the form of an insert or packaging which describe how to use the present kit.

In another embodiment, the present invention provides an immunoassay method comprising the steps:

(i) incubating a liquid sample, which may contain an analyte, with a reagent mixture, wherein said reagent mixture comprises an immobilized capture antibody and a labeled reporter antibody and wherein said immobilized capture antibody and said labeled reporter antibody bind specifically to said analyte; and (ii) measuring a signal attributable to a complex (sandwich) formed by binding of said immobilized capture antibody and said labeled reporter antibody to said analyte, wherein said reagent mixture has been prepared by lyophilizing a liquid comprising said labeled reporter antibody in the presence of said immobilized capture antibody.

The liquid sample which may contain the analyte may be drawn from any source which is desired to be analyzed. For example, the liquid sample may be a body or other biological fluid, such as blood, plasma, saliva, etc. Alternatively, the liquid sample may be water sample obtained from a body of water, such as lake or river. The liquid sample may also prepared by dissolving or suspending a sample in a liquid, such as water or an aqueous buffer. The liquid sample may be subjected to a treatment or processing, such as filtration or pH adjustment, prior to incubation. The liquid sample may further comprise or have added to it an agent which facilitates the generation or detection of the signal attributable to the complex formed by binding of the immobilized capture antibody and the labeled reporter antibody to the analyte. For example, when the reporter antibody is labeled with an enzyme, the liquid sample may further comprise or have added to it a substrate for that enzyme.

The incubation time is typically on the order of minutes, preferably less than 60 minutes, more preferably 1 to 30 minutes. Usually, the incubation is carried out at a temperature above 0° C. and below 50° C., preferably at about room temperature, but it is possible to perform the incubation at elevated or depressed temperatures by means of a heating or cooling bath. The incubation may be carried out with stirring or with agitation by means of a stirrer or shaker.

The exact steps and means of detecting the signal attributable to the complex formed by the binding of the immobilized capture antibody and the labeled reporter antibody to the analyte will depend on the exact nature of the labeled reporter antibody and possible the support on which the capture antibody is immobilized. Such techniques are well known in the art. For example, if the reporter antibody is labeled with a radioactive atom, then the signal may be detected by means of a scintillation counter.

In a preferred embodiment, the capture antibody is immobilized on a paramagnetic bead and the reporter antibody is labeled with ruthenium and the generation and detection of an electrochemiluminescent signal is relied upon to identify and/or quantify the presence of the analyte. Detection platforms which utilize electrochemiluminescence in conjunction with sandwich immunoassays are well know and are described in U.S. Pat. Nos. 5,962,218; 5,945,344; 5,935,779; 5,858,676; 5,846,485; 5,811,236; 5,804,400; 5,798,083; 5,779,976; 5,770,459; 5,746,974; 5,744,367; 5,731,147; 5,720,922; 5,716,781; 5,714,089; 5,705,402; 5,700,427; 5,686,244; 5,679,519; 5,643,713; 5,641,623; 5,632,956; 5,624,637; 5,610,075; 5,597,910; 5,591,581; 5,543,112; 5,466,416; 5,453,356; 5,310,687; 5,296,191; 5,247,243; 5,238,808; 5,221,605; 5,189,549; 5,147,806; 5,093,268; 5,068,088; and 5,061,445; in and Dong, L. et al, *Anal. Biochem.*, vol. 236, pp. 344–347 (1996); Blohm, et al, *Biomedical Products*, vol. 21, No. 4: 60 (1996); Jameison, F., et al, *Anal. Chem.*, vol. 68, pp. 1298–1302 (1996); Kibbey, M. et al, *Nature Biotechnology*, vol.14, no. 3, pp. 259–260 (1996); Yu, H., et al, *Applied and Environmental Microbiology*, vol. 62, no. 2, pp. 587–592 (1996); Williams Richard, Ph.D., *American Biotechnology*, page 26 (January, 1996); Darsley, M., et al, *Biomedical Products*, vol. 21, no. 1, p. 133 (January, 1996); Kobrynski, L., et al, *Clinical and Diagnostic Laboratory Immunology*, vol. 3, no. 1, pp. 42–46 (January 1996); Williams, Richard, Ph.D. *IVD Technology*, pp.28–31 (November, 1995); Deaver, D. R., *Nature*, vol. 377, pp. 758–760 (Oct. 26, 1995); Yu, H., et al, *BioMedical Products*, vol. 20, no. 10, p. 20 (October, 1995); Kibbey, M., et al, *BioMedical Products*, vol. 20, no. 9, p. 116 (September, 1995); Schutzbank, T. E., et al, *Journal of Clinical Microbiology*, vol. 33, pp. 2036–2041 (August, 1995); Stem, H. J., et al, *Clinical Biochemistry*, vol. 28, pp. 470–472 (August, 1995); Carlowicz, M., *Clinical Laboratory News*, vol. 21, no. 8, pp. 1–2 (August 1995); Gatto-Menking, D. L., et al, *Biosensors & Bioelectronics*, vol. 10, pp. 501–507 (July, 1995); Yu, H., et al, *Journal of Bioluminescence and Chemiluminescence*, vol. 10, pp. 239–245 (1995); Van Gemen, B., et al, *Journal of Virology Methods*, vol. 49, pp. 157–168 (1994); Yang, H., et al, *Bio/Technology*, vol. 12, pp. 193–194 (1994); Kenten, J. H., et al, *Clinical Chemistry*, vol. 38, pp. 873–879 (1992); Kenten, J. H., "Electrochemiluminescence," in *Non-radioactive Labeling and Detection of Biomolecules*, Kessler, Ed., Springer, Berlin, pp. 175–179 (1992); Gudibande, S., et al, *Journal of Molecular and Cellular Probes*, vol. 6, pp. 495–503 (1992); Kenten, J. H., et al, *Clinical Chemistry*, vol. 37, pp. 1626–1632 (1991); Blackburn G. F., et al, *Clinical Chemistry*, vol. 37, pp. 1534–1539 (1991), all of which are incorporated herein by reference.

After the signal attributable to the complex formed by the binding of the immobilized capture antibody and the labeled reporter antibody to the analyte has been detected, the presence and/or amount of the analyte may be determined by comparing a property of the detected signal, e.g., intensity, amplitude, etc., to a known or previously measured correlation between that property and the presence or the amount of the analyte.

The following provides a further description of the present reagents, kits, and methods in the context of a particularly preferred embodiment, referred to as the ECL FASTube immunoassay. However, it is to be understood that the present invention is not so limited.

The ECL FASTube immunoassay is based on the ability of freeze drying capture and reporter antibodies as well as an immunomagnetic 2.8 µm polystyrene bead concurrently in a single tube. In particular, various blocking procedures were incorporated into the ECL FASTube immunoassay in an effort to enhance assay sensitivity due to the non-specific binding activities of the paramagnetic bead inherent in the ECL assay. These studies focused on attempts to prevent nonspecific binding of the ruthenium-labeled antibody to the polystyrene surface of the paramagnetic bead. Nonspecific binding of the ruthenium-labeled antibody and bead while in solution and during the lyophilization process caused higher background ECL signals in the present ECL immunoassay format. Experimentation revealed that the reporter antibody was indiscriminately binding to the bead surface, thereby, driving the background ECL for the immunoassays in the range of 20,000 ECL units. The feasibility of producing a one-step antigen assay was investigated from the aspect of treating the paramagnetic beads by coating them initially with some form of blocking agent before the lyophilization process. This work involved the (1) selection of the blocking agents to use for the ECL immunoassays, (2) the determination of the efficiency of each blocking candidate in terms of percentage incorporation of the blocking agent into the assay, (3) the determination of percent reduction on assay background, (4) the selection of the most desirable format for the blocking step, and (5) the comparison of assay sensitivities with respect to Signal to Noise ratios for each blocking agent. The initial effort began with the ECL gold standard assay for *Bacillus subtilis var. niger* (BG) which was developed using the current ECL immunoassay format. The BG ECL assay was selected as the model assay for development of FASTube assay concept. The standard assay wet chemistry results were used as the gold standard reference point for all subsequent experimental evaluations. The preparation of anti-BG biotin and anti-BG ruthenium antibody conjugates was performed in a manner consistent with standard protocols used for labeling IgG for ECL use. The molar incorporation ratio (MIR) of goat anti-BG biotin was 3.58 at 0.53 mg/ml and goat anti-BG ruthenium was 9.8 at a concentration of 0.60 mg/ml.

Figure 1B:
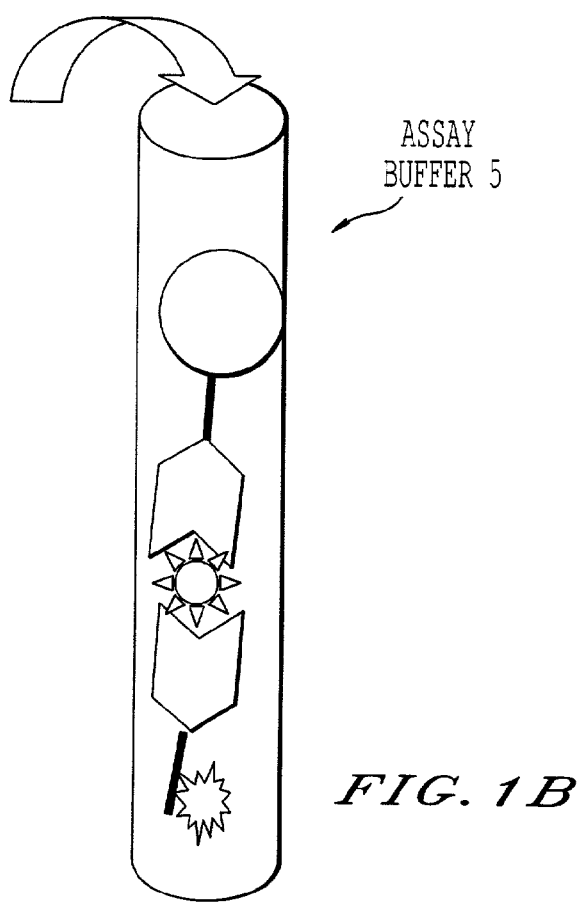
Figure 2A:
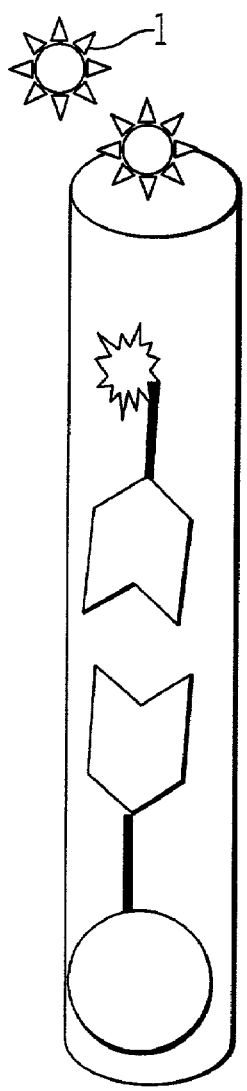
FIG. 2 is a schematic representation of a preferred embodiment of the present assay.
Figure 2B:
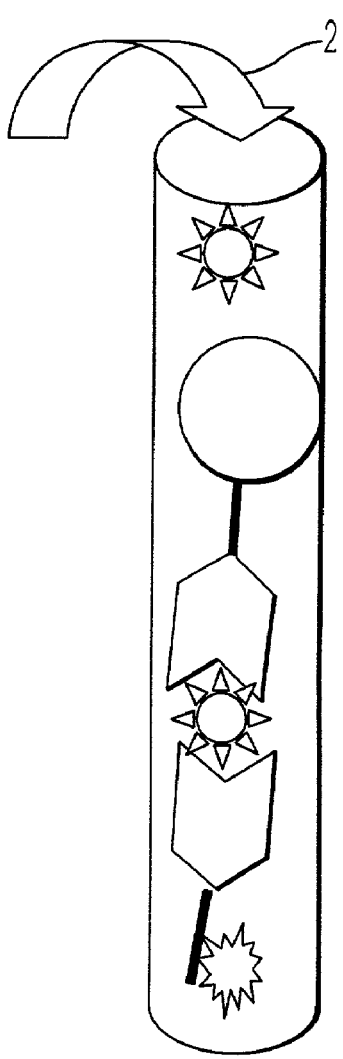
Figure 3:
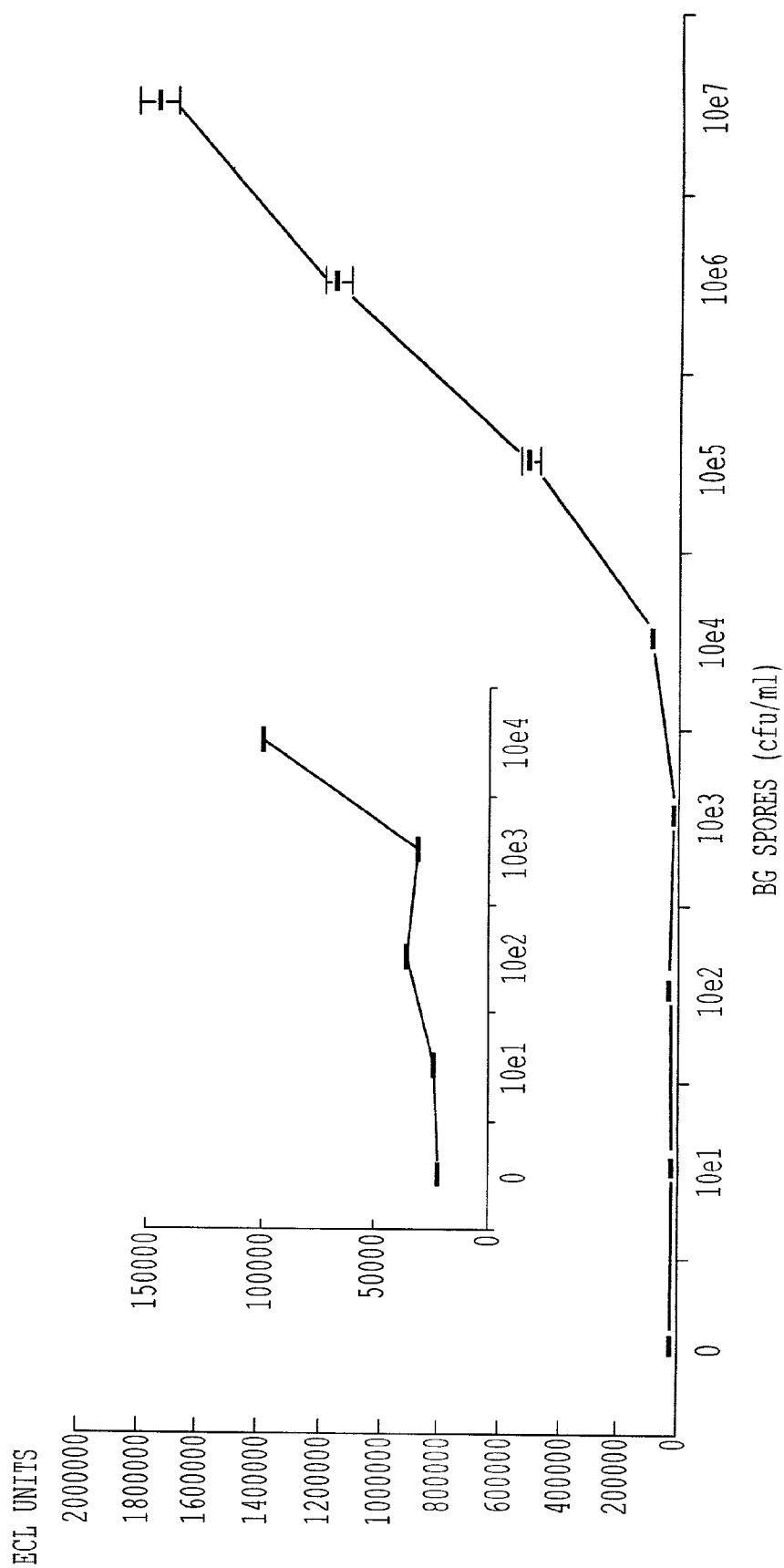
FIG. 3 is a graph which shows the ECL units as a function of BG spores (cfu/ml) resulting from the standard assay used for reference in the Examples.

The objective of the FASTube assay is to overcome the shortcomings of existing sandwich immunoassays by providing a device and method for immunoreagents wherein a qualitative or semi-quantitative assay can be performed easily with a one-step addition of sample in a plastic tube that is easy to handle. The inventors tailored the assay design to eliminate the dependence of numerous reagent vials and test tubes. There are no metric measurements or manual transfer of multiple reagents, pipette calibrations, etc. The inventors eliminated the necessity for extensive laboratory training for reagent preparation or handling and reduced the probability of a percentage of operator error due to pipetting manipulations, reagent transfer inaccuracies, and fixed-volume transfers. The inventors simplified overall assay procedures by eliminating complicated procedures and stringent reagent preparations. Operator handling and numerous user interactions were reduced to decrease the probability of end user error in clinical, medical, or field test situations. The invention combines the present ECL assay chemistries for inclusion into a self-contained, stand-alone plastic tube as opposed to numerous reagent combinations in the current assay format. The FASTube assay protocol is a simple one-step procedure that precludes the necessity for extensive laboratory training. The FASTube design is more cost effective and simplifies overall assay procedures. The method provides a rapid, sensitive, and uncomplicated assay format that requires only the addition of sample to a lyophilized product. FIG. 1 describes the conventional ECL immunoassay. FIG. 2 describes the improved FASTube assay compared to the conventional immunoassay shown in FIG. 1. As an example, the conventional ECL immunoassay construct requires five separate additions of assay constituents to a test tube with two separate incubation periods. The assay requires at least four pipetter calibrations for volume and multiple manipulations of immunoassay reagents. If the capture and reporter antibodies are in a lyophilized state, then reconstitution of each requires two more steps to the process or a total of seven additions. The assay format is performed as follows (refer to FIG. 1): a pipetter is adjusted to a specified amount of biotinylated capture antibody 1 to pipette into a test tube, followed by the addition of a specified volume of ruthenium-labeled reporter antibody 2 into the same tube. Next the pipetter is recalibrated to deliver a specified amount of antigen 3 into the tube, and the immunocomplex is incubated for approximately 25 minutes. After the incubation period, a specified volume of streptavidin-coated paramagnetic bead is introduced into the complex 4, followed by a 10-minute incubation. The final step 5 is the addition of a specified volume of ECL assay buffer for the reaction. The FASTube immunoassay requires only the addition of antigen to a test tube with one incubation period. All assay constituent concentrations have been optimized for lyophilization in a single 12×75 mm polypropylene reaction tube. Each FASTube contains a specified amount of biotinylated capture antibody, a specified volume of ruthenium-labeled reporter antibody, and a specified volume of streptavidin-coated paramagnetic bead. The end user simply delivers a specified amount of antigen into the tube 1, and the immunocomplex is incubated for approximately 10–15 minutes, after which assay buffer 2 is added to the tube and the ECL is read (refer to FIG. 2).

The present immunoassay eliminatew the separate pipette measurements and additions necessary for the (1) specified amount of biotinylated capture antibody (2) specified amount of ruthenium-labeled reporter antibody (3) specified volume of antigen (4) incubation of immunocomplex (5) addition of specified volume of paramagnetic bead, (6) a separate incubation step required after the addition of the bead to the immunocomplex, and (7) specified volume of assay buffer.

Figure 12A:
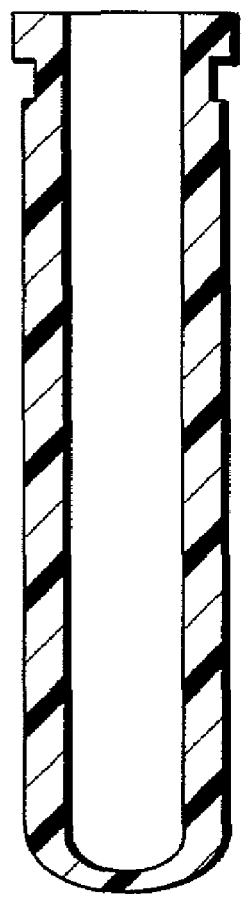
FIG. 12 is a schematic representation of a device used in the Examples.
Figure 12B:
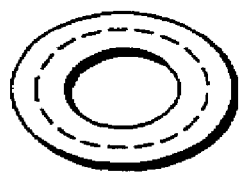

The simplicity of the present immunoassay has been enhanced by the ability to lyophilize all necessary assay constituents in a specially designed 12×75 mm polypropylene test tube that is capable of being hermetically sealed until use (refer to FIG. 12). In this case, a biotinylated capture antibody, ruthenium-labeled reporter antibody, and 2.8 μm polystyrene immunomagnetic bead are freeze dried simultaneously in a single tube. To test for the presence of biological material in a sample, the end user places the one-step assay tube in the ECL carousel and reconstitutes the tube contents with a specified volume of antigen sample, followed by a short incubation period (10–15 minutes). Once the incubation is complete, an aliquot of assay buffer containing tripropylamine (used solely for ECL assays) is added to the test tube and a photomultiplier tube in the analyzer reads the electrochemiluminescence. The entire assay time is approximately 15 minutes.

Other features of the invention will become apparent in the course of the following descriptions of exemplary embodiments which are given for illustration of the invention and are not intended to be limiting thereof.

EXAMPLES

I. Protocols.

The following protocols were used throughout the Examples described below.

1. Protocol 1: Standard Lyophilization Procedure for FASTube Preparation

Materials and Equipment:
  Dura-Top Microprocessor Freeze Dryer. FTS Systems
  Ruthenium anti-BG conjugate product
  Biotin anti-BG conjugate product
  Analytical balance (top loading or equivalent)
  Lyophilization vials—I ml clear
  Vortex Genie 2
  Butyl rubber lyophilization stopper, 13 mm
  Flip tear aluminum seal, 13 mm
  Eppendorf Repeater Pipette w/2.5 ml Combitip
  Disposable latex gloves
  Surgical mask
  70% alcohol Method:
1. Lyophilization material is placed into vials in the following manner:
   a. Use an area dedicated to filling vials only.
   b. Wipe area surface with 70% alcohol
   c. Arrange clean, dust free vials for easy access and filling.
2. Calibrate filling apparatus to fill within the following specifications:
   a. Assume 1 gm=1 ml
   b. Specification: Mean=0.048 to 0.052 ml CV=≦2%
   c. Record calibration data
   d. Demonstrate a minimum of 10 data points
   e. Calculate the mean and % CV
   f. Adjust apparatus to meet fill specifications.
   g. Arrange vials in freeze dryer tray and begin filling operation.
   h. Stir antibody conjugate lyophilization mixture frequently.
   i. Keep antibody conjugate lyophilization mixture cool during filling operation.
   j. Insert one butyl rubber stopper into each vial.
   k. Insert only to first indentation on stopper prong.
   l. Stopper must not be tight so that vapor can escape during freeze drying.
3. Load the freeze dryer in the following manner:
   a. Load trays onto 2° to 10° C. freeze dryer shelves
   b. Insert thermocouples into the appropriate vial (100 μl of 1× lyophilization buffer)
   c. Check thermocouple attachments to freeze dryer.
   d. Thermocouple should not touch bottom or sides of glass vial but should be immersed in solution.
2. Protocol 2: Lyophilization Program

| | |
|---|---|
| PROG | |
| SELECT PROG | |
| FTm (freezing time) | 240 min |
| Pt# | |
| ST1 (1st temp primary drying) | −40 |
| VAC I (1st segment pressure) | 70 |
| TIM I (time to hold 1st temp) | 960 min |
| ST 2 | −20 |
| VAC 2 | 70 |
| TIM 2 | 480 min |
| ST 3 | 0 |
| VAC 3 | 75 |
| TIM 3 | 480 min |
| ST 4 | 20 |
| VAC 4 | 75 |
| TIM 4 | 120 |
| PrTm (Print time) | 30 |
| Press SELECT | |
| Press START | |

3. Protocol 3: FASTube Assay Protocol (15-minutes)

Uncap and place a FASTube Assay Antigen test in ECL carousel. Add specified amount of antigen sample to the FASTube and incubate for 10–15 minutes. Add 200 μm of assay buffer to FASTube and read ECL.

Figure 4A:
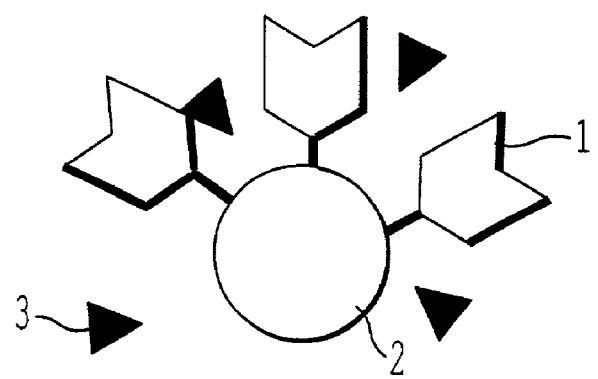
FIGS. 4A and 4B are schematic representations of Blocking Format A and Blocking Format B, respectively.
Figure 4B:
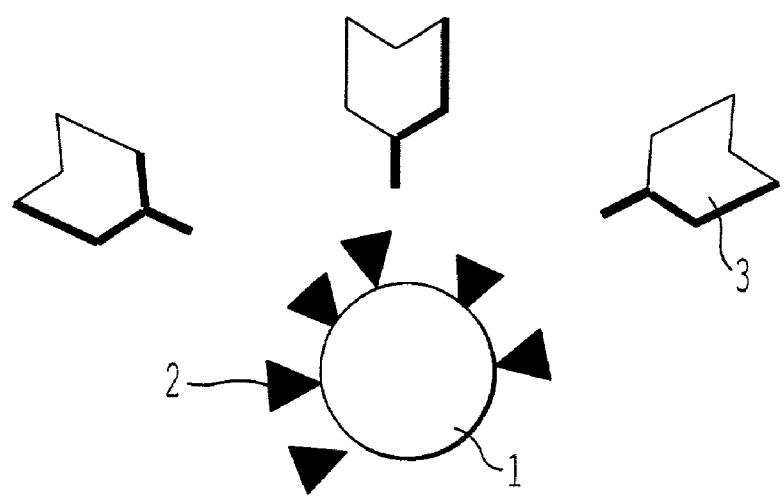

4. Protocol 4: Format A Reagent Preparation
1. Prepare 48 tests per blocking series at 0%, 5%, 10%, 20%, 30%, 50% (v/v)
   a. 3 replicates×7 antigen dilutions+background=24 tests
   b. Prepare reagent for 2 ECL runs at 24 tests per run=48 tests
   c. Allow 15% excess reagent for vial filling (48 tests× 0.15)=7.2 tests
   d. Therefore, prepare 55 test's worth of reagent
   e. Total volume of reagent needed (55 tests×0.05 ml per tube) or 2.75 ml per series
2. Determine Dynabead incorporation at 20 μg per test. Concentration of beads per vial is 20 μg per vial×55 vials or 1.1 mg of beads needed
   a. Stock concentration of Dynabeads M-280 is 1 ml at 10 mg/ml
   b. Therefore, 0.11 ml of beads are needed per series
   c. Determine volume of biotinylated goat anti-BG to incorporate into series at 100 ng/test
   d. Stock concentration of biotin conjugate is 530 μg/ml
   e. Therefore, 55 tests @ 0.1 μg per test=10.3 μl of biotin conjugate per series 3. Determine volume of ruthenium goat anti-BG to incorporate into series at 100 ng/test
   a. Stock concentration of ruthenium conjugate is 602 μg/ml
   b. Therefore, 55 tests at 0.1 μg per test=9.1 μl of ruthenium conjugate per series 5. Protocol 5: Format B Reagent Preparation
1. Prepare 24 tests per blocking series: 3 replicates×8 antigen dilutions=24 tests
   a. Prepare reagent for 1 ECL run @ 24 tests per run=24 tests
   b. Allow 15% excess reagent for vial filling (24 tests×0.15)=3.6 tests
   c. Therefore, prepare 30 test's worth of reagent
   d. Total volume of reagent needed (30 tests×0.05 ml per vial) or 1.5 ml per series
2. Determine Dynabead incorporation at 20 μg per test
   a. Concentration of beads per vial is 20 μg per vial×30 vials or 0.6 mg of beads needed
   b. Stock concentration of Dynabeads M-280 is 1 ml at 10 mg/ml
   c. Therefore, 0.06 ml of beads are needed per series
3. Determine volume of biotinylated goat anti-BG to incorporate into series @ 100 ng/test
   a. Stock concentration of biotin conjugate is 530 μg/ml
   b. Therefore. 30 tests @ 0.1 μg per test=6.0 μl of biotin conjugate per series
4. Determine volume of ruthenium goat anti-BG to incorporate into series @ 100 ng/test
   a. Stock concentration of ruthenium conjugate is 602 μg/ml
   b. Therefore, 30 tests @ 0.1 μg per test=5.0 μl of ruthenium conjugate per series 6. Protocol 6: *C. botulinum* A and *Escherichia coli* 0157 Reagent Preparation
1. Prepare 500 FASTube tests beginning with 50% Blotto suspension for pre-blocking Dynabeads at 10.4% prior to lyophilization
   a. Total volume of reagent needed (500 tests×0.05 ml per tube ) or 25 ml each for BoTx and *E. coli* FASTube
   b. Determine Dynabead incorporation at 20 μg per test. Concentration of beads per test is 20 μg per test×500 tests or 10 mg of beads needed
   c. Stock concentration of Dynabeads M-280 is 2 ml at 10 mg/ml (IGEN Cat. #402-175-01, lot 7119)
   d. Therefore, 1 ml of beads are needed per assay (1 vial)
2. Determine volume of biotinylated goat anti-BoTx to incorporate into series at 50 ng/test
   a. Stock concentration of biotin anti-BoTx conjugate is 250 μg/ml
   b. Therefore, 500 tests at 0.05 μg of biotin conjugate per test=100 μl of biotin anti-BoTx conjugate needed
3. Determine volume of biotinylated goat anti-*E. coli* to incorporate into series at 50 ng/test
   a. Stock concentration of biotin anti-*E. coli* conjugate is 280 μg/ml
   b. Therefore, 500 tests at 0.05 μg of biotin conjugate per test=89.2 μl of biotin anti-*E. coli* conjugate needed
4. Determine volume of ruthenium goat anti-BoTx to incorporate into series at 50 ng/test
   a. Stock concentration of ruthenium anti-BoTx conjugate is 170 μ/ml
   b. Therefore, 500 tests at 0.05μ per test=147 μl of ruthenium conjugate
5. Determine volume of ruthenium goat anti-*E. coli* to incorporate into series at 50 ng/test
   a. Stock concentration of ruthenium anti-*E. coli* conjugate is 220 μg/ml
   b. Therefore, 500 tests at 0.05 μg per test=113.6 μl of ruthenium conjugate 7. Protocol 7: BG FASTube Reagent Preparation 1. Prepare 1400 BG FASTube tests beginning with 50% Blotto suspension for pre-blocking Dynabeads at 10.4% prior to lyophilization.
   a. Total volume of reagent needed (1400 tests×0.05 ml per tube) or 70 ml for the BG FASTube
   b. Determine Dynabead incorporation at 20 μg per test. Concentration of beads per test is 20 μg per test×1400 tests or 28 mg of beads needed
   c. Stock concentration of Dynabeads M-280 is 2 ml at 10 mg/ml (IGEN Cat. #402-175-01, lot #7119)
   d. Therefore, 2.8 ml of beads are needed (2 vials)
2. Determine volume of biotinylated goat anti-BG to incorporate into assay at 50 ng/test
   a. Stock concentration of biotin anti-BG conjugate is 180 μg/ml
   b. Therefore, 1400 tests at 0.05 μg of biotin conjugate per test=389 μl of biotin anti-BoTx conjugate needed
3. Determine volume of ruthenium goat anti-BG to incorporate into assay at 50 ng/test
   a. Stock concentration of ruthenium anti-BG conjugate is 250 μg/ml
   b. Therefore, 1400 tests at 0.05 μg per test=280 μl of ruthenium conjugate

II. EXAMPLES

Preparation of Antibody and Antigen Dilutions

Goat anti-BG biotin and ruthenium conjugates were diluted in 1× Threshold (THS) assay buffer for ECL analysis. An antibody load was determined based upon historical data and experience using this antibody. Biotinylated and ruthenium labeled antibodies were incorporated into the assay at 100 ng/test. BG spore (at $1\times10^{11}$ cfu/ml) dilutions were prepared in 0.01M PBS+0.05% $NaN_3$ for a stock concentration of $1\times10^{7}$ cfu/ml. The subsequent dilutions were made in I×THS assay buffer in final concentrations of $1\times10^{6}$ cfu/ml to $1\times10^{1}$ cfu/ml. Spore preparations were stored at 4° C. for the test duration.

ECL Standard Assay Protocol

All experiments performed for ECL detection were 15 minute assays. Initially, 25 μl of each labeled antibody was placed into a 12×75 mm test tube along with 50 μl of the respective BG antigen dilution (ECL assay buffer for negative control) and gently vortexed for 10 minutes at 70 rpm. Dynabead M-280 Streptavidin (Cat. #402-175-01) at 1 mg/ml was added at a volume of 20 μl and the immunocomplex was vortexed for 5 minutes at 70 rpm, followed by the addition of 150 μl of ECL assay buffer. The ECL measurement was taken and the Signal to Noise ratio was calculated along with statistical analyses. Three replicate data points were generated for each BG antigen dilution. The standard deviation and % CV were derived from mean values of the BG dilution series. Detection cutoff was determined by dividing mean ECL signal response for each BG antigen dilution by the mean background value (20699 ECL units). Based upon the Signal to Noise ratio, the endpoint sensitivity for the BG assay was $1\times10^{4}$ cfu/ml (refer to Table 1). A linear response was obtained over a range of 4 logs ($10^{3}$ to $10^{7}$ cfu/ml). FIG. 3 demonstrates the standard assay for BG spores. The assay formats shown in FIG. 1 (conventional ECL immunoassay construct) and FIG. 2 (FASTube construct) are based on the capture of the labeled immune complexes containing the conjugated chelate to a solid phase consisting of magnetic beads. The conventional format requires no less than 5–6 separate steps to prepare the reagents for ECL analysis. The antibody conjugates are generally stored in liquid form until dilutions are made from stock. Freedom from contamination due to repeated removal of aliquots from the conjugate tube have been a concern. The FASTube approach provides one BG test per reaction tube in a lyophilized form. A polypropylene single use 12×75 mm lyophilization tube was designed for the capability of vacuum sealing under freeze drying conditions. Each reaction tube contains the specified amounts of antibody conjugates needed for the immunoreaction, as well as the appropriate amount of paramagnetic beads to elicit the desired ECL response. One hundred microliters of sample is added to the BG FASTube and incubated in the ECL carousel for 15 minutes, followed by the addition of 200 μl of ECL assay buffer for ECL responses Dynabead Blocking Experiments: Evaluation of Blocking Measures for Lowering Background Effects Throughout the history of assay development of immunoglobulins on the ECL analyzer, the issue of high background effects due to the nonspecific binding of ruthenium-labeled antibody was a consistent problem that needed to be addressed. During the freeze drying process, the reporter antibody had opportunity to adhere to the polystyrene surface of the Dynabead M-280. Two effects were a matter of concern in the optimization of ECL assays. First, nonspecific adherence to the bead surface drove the ECL background responses higher and lower detection sensitivities were compromised. Secondly, the random adherence of the reporter antibody during freeze drying would decrease the amount available for binding to antigen during the incubation step, thereby, compromising overall sensitivity determinations for the assay. Two blocking formats were designed for the lyophilization procedure: (1) Format A consisted of combination of the bead and biotinylated conjugate, followed by a blocking step with goat serum, goat IgG, or Blotto, and (2) Format B consisted of a bead pre-block with Blotto or goat IgG, followed by addition of biotin and ruthenium antibody conjugates. FIG. 4 represents both blocking formats used for FASTube preparation.

Blocking Formats A and B

FIG. 4 is the schematic representation of blocking procedures utilized for ECL one-step antigen FASTube immunoassay development. Format A consists of primary immobilization of biotinylated anti-BG conjugate 1 to Dynabead M-280 Streptavidin 2, followed by the addition of the blocking agent(s) 3 to bead. Format B introduces a preliminary bead pre-block of blocking agent 2, followed by the immobilization of anti-BG biotin conjugate ③ to the streptavidin-coated Dynabead 1.

Format A Bead Blocking Procedure Using Goat Serum @ 0–50%

A blocking step was designed to incorporate goat serum (Sigma Cat. G-9023, lot #034H8995) into the procedure at series 0%, 5%, 10%, 20%, 30%, and 50% (v/v). Dynal Dynabead M-280 Streptavidin (Product No. 112.05, lot #A5290) at 10 mg/ml was blocked sequentially during the process. An attempt was made to reproduce the standard assay reaction volume (1:5 ratio of bead to total volume in the reaction) for FASTube assay preparation. A total of 48 tests were prepared for each blocking series which would provide enough data for two runs of 3 replicates per 7 dilutions of BG spores (plus background) for each series. Protocol 4 describes the blocking procedure used for Format A. Once the reagents were prepared, six 5-ml polypropylene Falcon tubes were labeled with series numbers 0% to 50%. To each tube, 450 μl of 1× lyophilization buffer was added, followed by the addition of 10.3 μl of biotin anti-BG IgG with gentle vortex. While vortexing, 110 μl of Dynabead M-280 were added sequentially to the tube and incubated for 15 minutes at ambient room temperature (ART, approx. 26° C.). The bead-IgG complex was placed on a Nutator rotator for the incubation step to assure consistent suspension of the beads during incubation. At this point the volume per tube was 570.3 μl. After incubation, goat serum was added to respective tubes in the volumes indicated in Table 2. The Dynabead-IgG complex was incubated for 30 minutes at ART with gentle rocking on the rotator. The 30-minute incubation period was selected arbitrarily and was not based on any previous experience with this particular blocking format; however, if the block proved to be inefficient, future efforts would utilize longer blocking periods and/or blocking at 37° C. Up to this point each blocking series was made simultaneously; however, ruthenium anti-BG conjugate was added separately as each series was pipetted into the reaction vials for lyophilization. The lower percent series were filled first; therefore, ruthenium anti-BG was absent from the blocking series at 30% and 50% for a longer period of time than for series at 5% or 10% (time interval was approximately 30 minutes). Table 3 shows the final volume additions of ruthenium anti-BG conjugate and 1× lyophilization buffer to each series.

TABLE 1

Statistical Analysis of ECL BG Gold Standard Assay Results.

| BG cfu/ml | ECL | STD | % CV | S/N |
|---|---|---|---|---|
| 0 | 20699 | 1262.6 | 6.1 | |
| $10^1$ | 22999 | 1402.9 | 6.1 | 1.1 |
| $10^2$ | 35468 | 1631.5 | 4.6 | 1.7 |
| $10^3$ | 31270 | 1782.4 | 5.7 | 1.5 |
| $10^4$ | 99928 | 3497.5 | 3.5 | 4.8 |
| $10^5$ | 516532 | 32541.5 | 6.3 | 25 |
| $10^6$ | 1166294 | 46641.8 | 4 | 56.3 |
| $10^7$ | 1757479 | 63269.2 | 3.6 | 84.9 |

TABLE 2

Amount of Goat Serum Added to Dynabead-IgG Complex for Format A Blocking Step. Percent Block is based on Volume at 570.3 μL.

| Block Series % Goat serum | Goat serum | Final volume (μl) |
|---|---|---|
| 0 | 0 | 570.3 |
| 5 | 28.5 μl | 598.8 |
| 10 | 57 | 627.3 |
| 20 | 114 | 684.3 |
| 30 | 171 | 741.3 |
| 50 | 285 | 855.3 |

TABLE 3

Final Volume Additions of Ruthenium Anti-BG and 1X Lyophilization Buffer to Series.

| Block Series % Goat Serum | Volume after Block (μl) | Reporter anti-BG (μl) | 1X Lyophilization Buffer (ml) | Final Volume (ml) |
|---|---|---|---|---|
| 0 | 570.3 | 9.1 | 2.17 | 2.75 |
| 5 | 598.8 | 9.1 | 2.14 | 2.75 |
| 10 | 627.3 | 9.1 | 2.11 | 2.75 |
| 20 | 684.3 | 9.1 | 2.05 | 2.75 |
| 30 | 741.3 | 9.1 | 1.99 | 2.75 |
| 50 | 855.3 | 9.1 | 1.88 | 2.75 |

Lyophilization of FASTube Reagents

A standard lyophilization procedure was developed for use with FASTube assay development.

Figure 5:
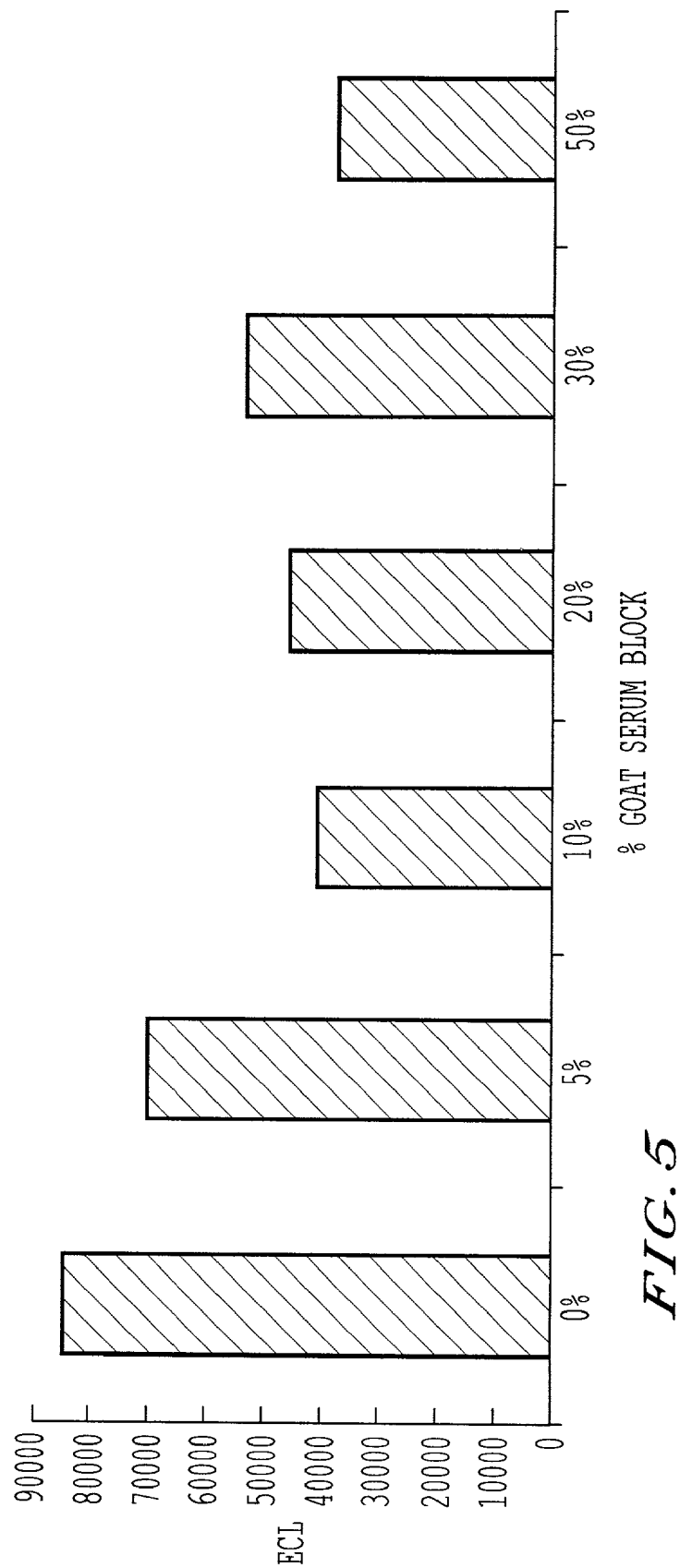
FIG. 5 is graph which shows the ECL units as a function of % goat serum block resulting from an experiment reported in the Examples.

Results of Goat Serum Block Subsequent to Biotin Anti-BG Conjugate Immobilization to Dynabead Following freeze drying, each series of lyophilized product was evaluated using a 15-minute FASTube protocol. Background ECL units and endpoint sensitivities were used to determine the effectiveness of using goat serum from 0% to 50% in FASTube assay formats for reduction of nonspecific adherence to the Dynabead. Fresh BG spore dilutions were prepared from $1 \times 10^7$ cfu/ml to $1 \times 10^1$ cfu/ml in 1× Threshold assay buffer. The FASTube assay protocol for ECL measurement is described in Protocol 3. Table 4 describes the ECL responses for BG FASTube assay series blocked with goat serum percentages using Format A. Mean values from three replicates are shown for BG spore dilutions. Signal to Noise Ratios were calculated by dividing the net signal by the background responses. The bead block with goat serum demonstrated a lower background with no loss of sensitivity for 5% to 50% blocks. The data suggest that goat serum incorporations from 10% to 50% yield basically the same blocking effectiveness with the exception of the 30% block which gave a background response that was somewhat higher. Signal to Noise Ratios for BG spores at $1 \times 10^4$ cfu/ml were higher for heavier serum blocks at 20% to 50%. Signal to Noise Ratios for 0% and 5% blocks were 2.5 to 3.0. Bead blocks from 20% to 50% yielded Signal to Noise Ratios of 3.5 to 4.0 at the sensitivity cutoff. The overall decrease in background by using a goat serum block is reported by percent reduction: 5% block at 17% reduction, 10% block at 52% reduction, 20% block at 45% reduction, 30% block at 36% reduction, and 50% block at 55% reduction. FIG. 5 describes the relationship.

combining 1 gm of Sigma BSA in 8 ml of Nanopure $H_2O$ with gentle stirring and final adjustment to 10 ml with water. Sigma goat serum (Cat. #G-9023, lot #034H8995) was incorporated at 50% blocks in the evaluation. Dynabead M-280 Streptavidin paramagnetic beads (IGEN, Cat. #402-125-01, lot #7030) at 10 mg/ml were used for the evaluation. Four 5-ml Falcon polypropylene tubes were labeled with blocked designations. To each tube, 450 µl of 1× lyophilization buffer was added, followed by the addition of 10.3 µl of biotin anti-BG IgG with gentle vortex. While vortexing, 110 µl of Dynabead M-280 was added sequentially to the tube and incubated for minutes at ambient room temperature (ART, approx. 26° C.). The bead-IgG complex was placed on a Nutator rotator for the incubation step to assure consistent suspension of the beads during incubation. At this point the volume per tube was 570.3 µl. After incubation blocking constituents were added to respective tubes in the volumes indicated in Table 5. The Dynabead-IgG complex was incubated for 30 minutes at ART with gentle rocking on the rotator. The 30-minute incubation period was selected arbitrarily and was not based on any previous experience with this particular blocking format; however, if the block proved to be inefficient, future efforts would utilize longer blocking periods and/or blocking at 37° C. Up to this point each blocking series was made simultaneously; however, ruthenium anti-BG conjugate was added separately as each series was pipetted into the serum vials for lyophilization. Table 6 shows the final volume additions of ruthenium anti-BG conjugate and 1× lyophilization buffer to each series. The reagents were lyophilized using protocols 1 and 2.

TABLE 4

ECL Net Signal Responses for BG FASTube Assay.

| Series % Block | ECL 0 | ECL $10^1$ | ECL $10^2$ | ECL $10^3$ | ECL $10^4$ | ECL $10^5$ | ECL $10^6$ | ECL $10^7$ |
|---|---|---|---|---|---|---|---|---|
| 0% | 84077 | 115193 | 112474 | 119773 | 256431 | 843451 | 1641989 | 1654482 |
| 5% | 69642 | 64042 | 61913 | 84896 | 182509 | 566075 | 1478014 | 1798855 |
| 10% | 40449 | 51935 | 55264 | 71898 | 157726 | 609160 | 1528650 | 1735856 |
| 20% | 45871 | 39131 | 51044 | 63332 | 165970 | 581121 | 1344075 | 1572903 |
| 30% | 53437 | 56732 | 59242 | 120232 | 207324 | 676591 | 1348730 | 1659826 |
| 50% | 37788 | 41352 | 49681 | 58996 | 132362 | 520627 | 1238125 | 1520585 |

Format A Bead Blocking Procedure Using Goat Serum at 50%, Blotto at 25%, and BSA at 5%

The results from the 0% to 50% goat serum block were encouraging, therefore, the follow-on evaluation focused on incorporating two other blocking agents that were also under consideration, as well as, repeating the experiment using goat serum blocks at 50%. A 50% Blotto suspension (w/v) was prepared by placing 5 gm of Carnation Nonfat Dry Milk into 8 ml of Nanopure $H_2O$. The mixture was stirred and adjusted to 10 ml final volume with $H_2O$. A 10% Bovine Serum Albumin (BSA) solution (w/v) was prepared by

TABLE 5

Amount of Blocking Constituent Added to Dynabead-IgG Complex for Format A Blocking Step. Percent Block is Based on Volume at 570.3 µl

| Blocking Constituent (v/v) | Blocking Agent Addition (µl) | Final Incubation Volume (µl) |
|---|---|---|
| Goat Serum 50% | 570.3 | 1140.6 |
| Blotto 25% | 570.3 | 1140.6 |
| BSA 5% | 570.3 | 1140.6 |

TABLE 6

Final Volume Addition of Ruthenium Anti-BG and 1X Lyophilization Buffer to Series.

| Blocking Agent | Volume after Block (μl) | Ruthenium anti-BG (μl) | 1X Lyophilization Buffer (ml) | Final Volume (ml) |
|---|---|---|---|---|
| Goat Serum | 1140.6 | 9.1 | 1.6003 | 2.75 |
| Blotto | 1140.6 | 9.1 | 1.6003 | 2.75 |
| BSA | 1140.6 | 9.1 | 1.6003 | 2.75 |

Results of 50% Goat Serum, 25% Blotto, and 5% BSA Block

Figure 6:
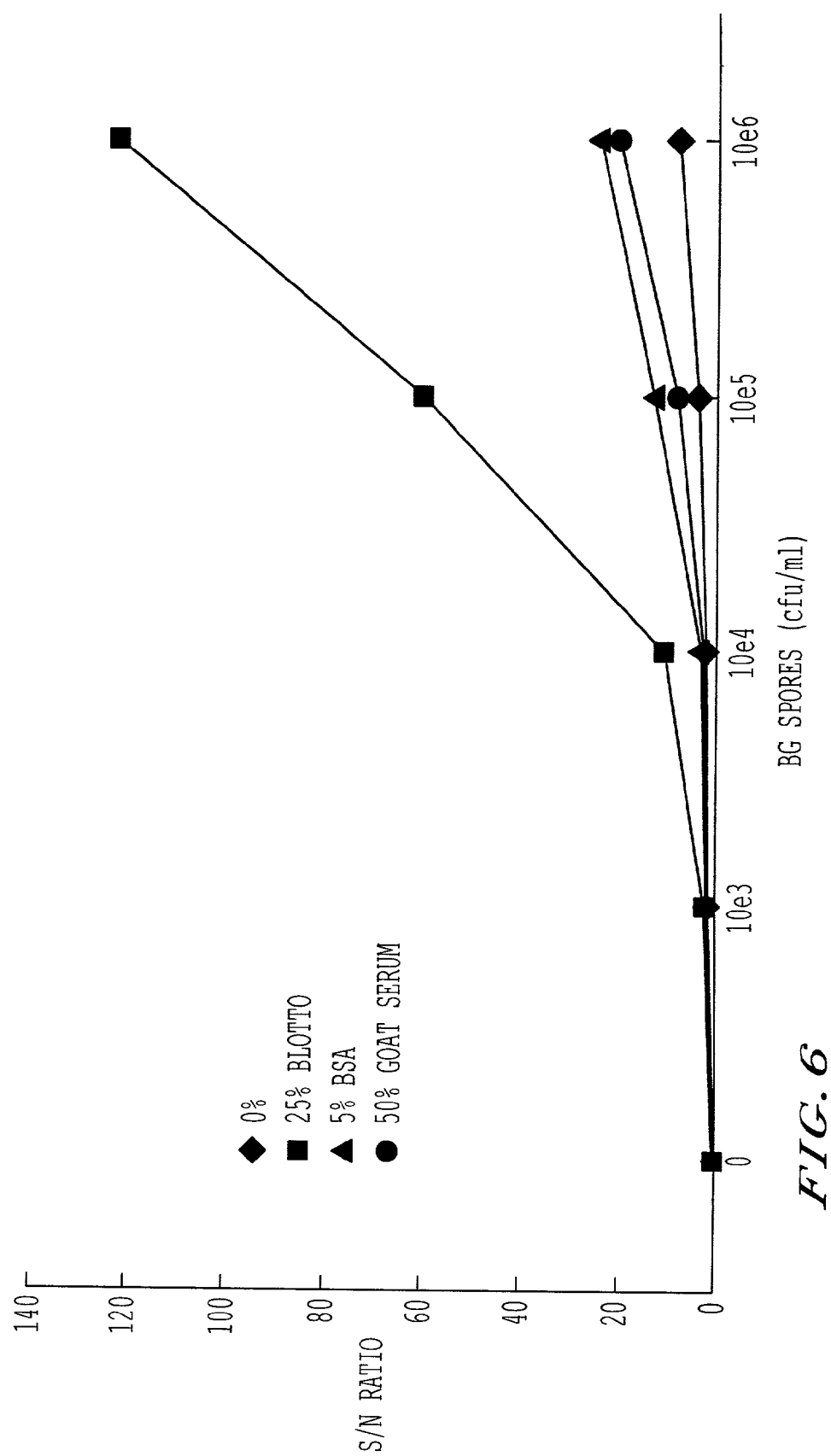
FIG. 6 is graph which shows the signal to noise (S/N) ratio as a function of BG spores (cfu/ml) resulting from an experiment reported in the Examples.
Figure 7:
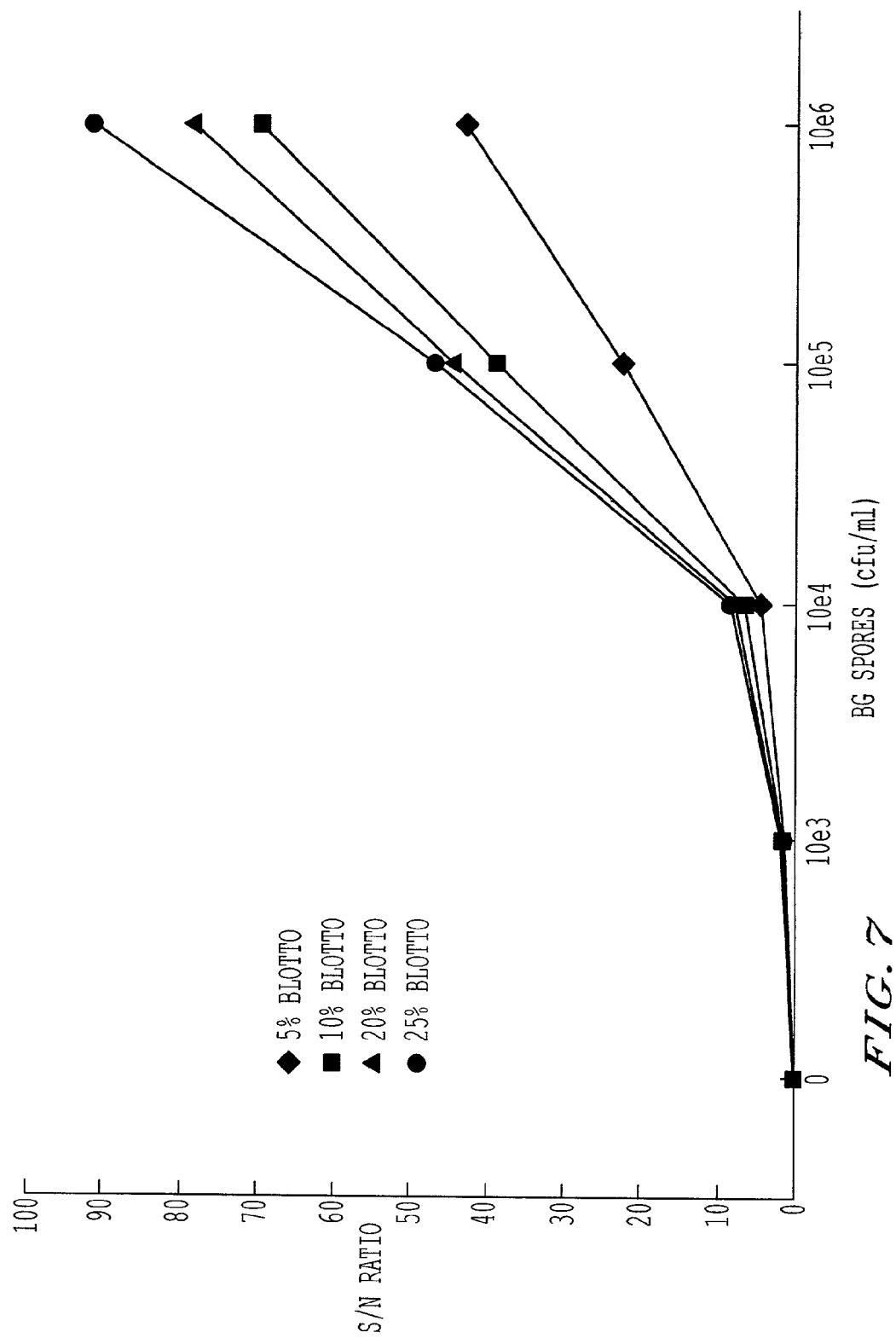
FIG. 7 is graph which shows the signal to noise (S/N) ratio as a function of BG spores (cfu/ml) resulting from an experiment reported in the Examples.
Figure 8:
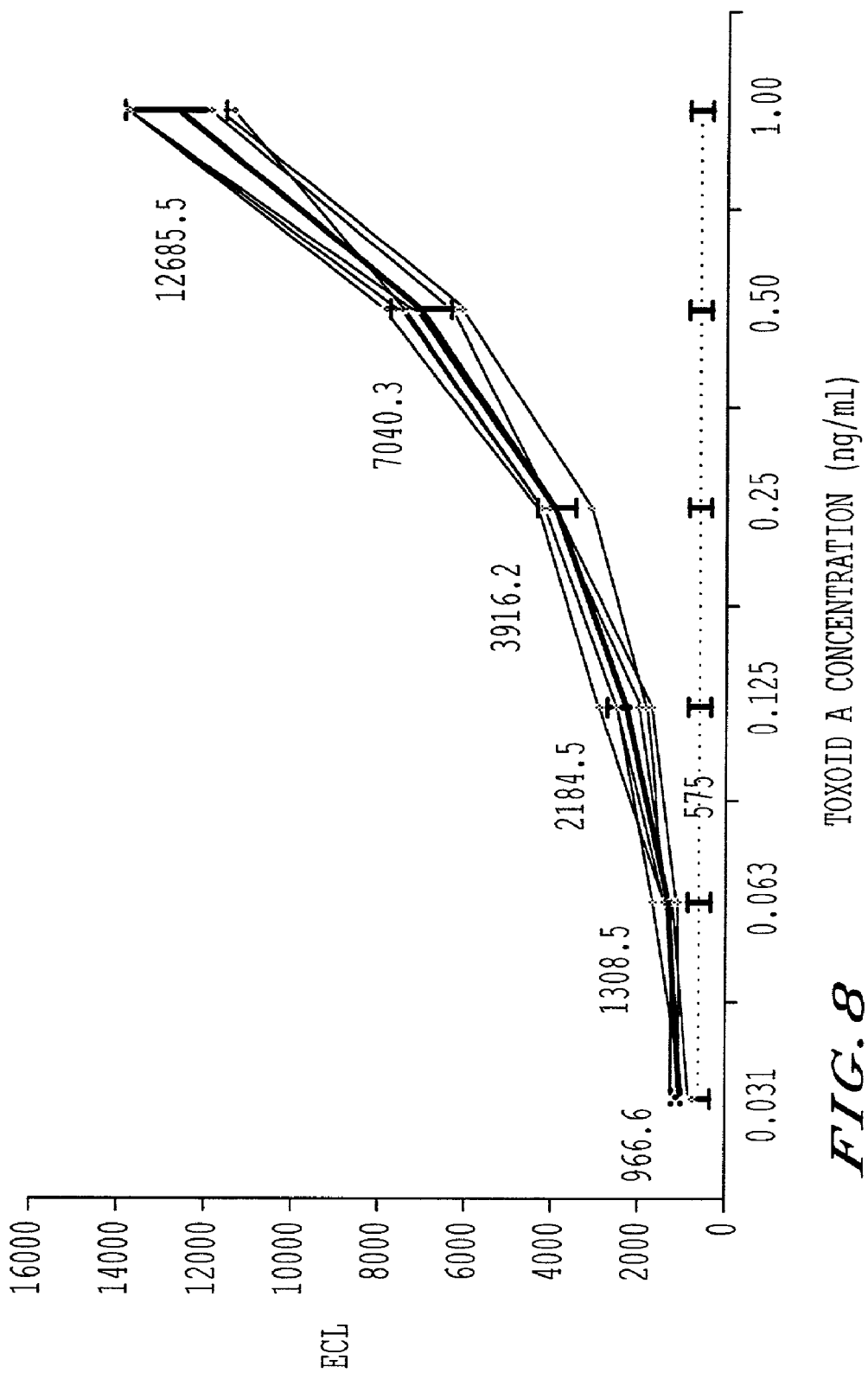
FIG. 8 is graph which shows the ECL units as a function of Toxoid A concentration (ng/ml) resulting from an experiment reported in the Examples.
Figure 9:
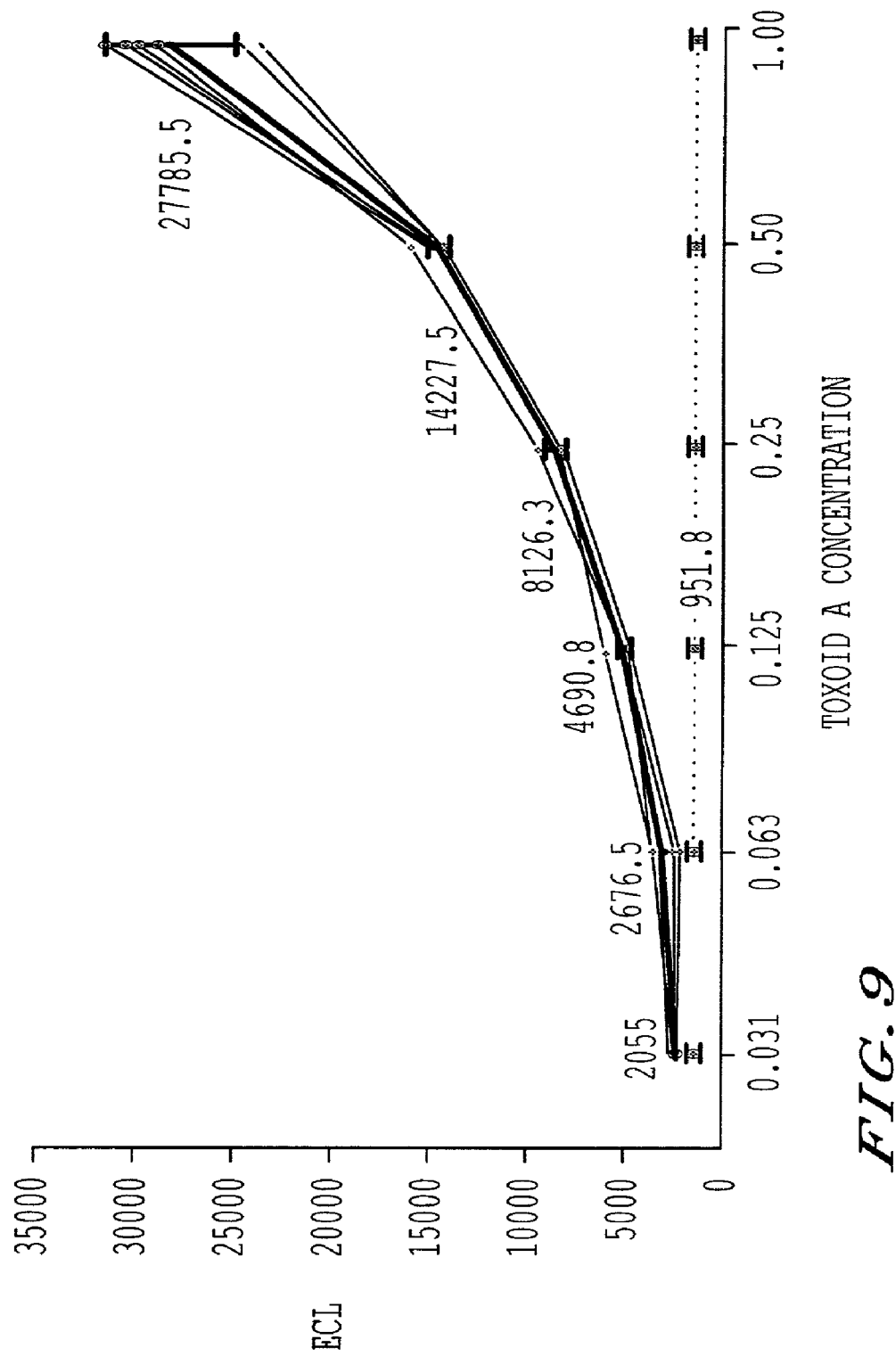
FIG. 9 is graph which shows the ECL units as a function of Toxoid A concentration (ng/ml) resulting from an experiment reported in the Examples.
Figure 10:
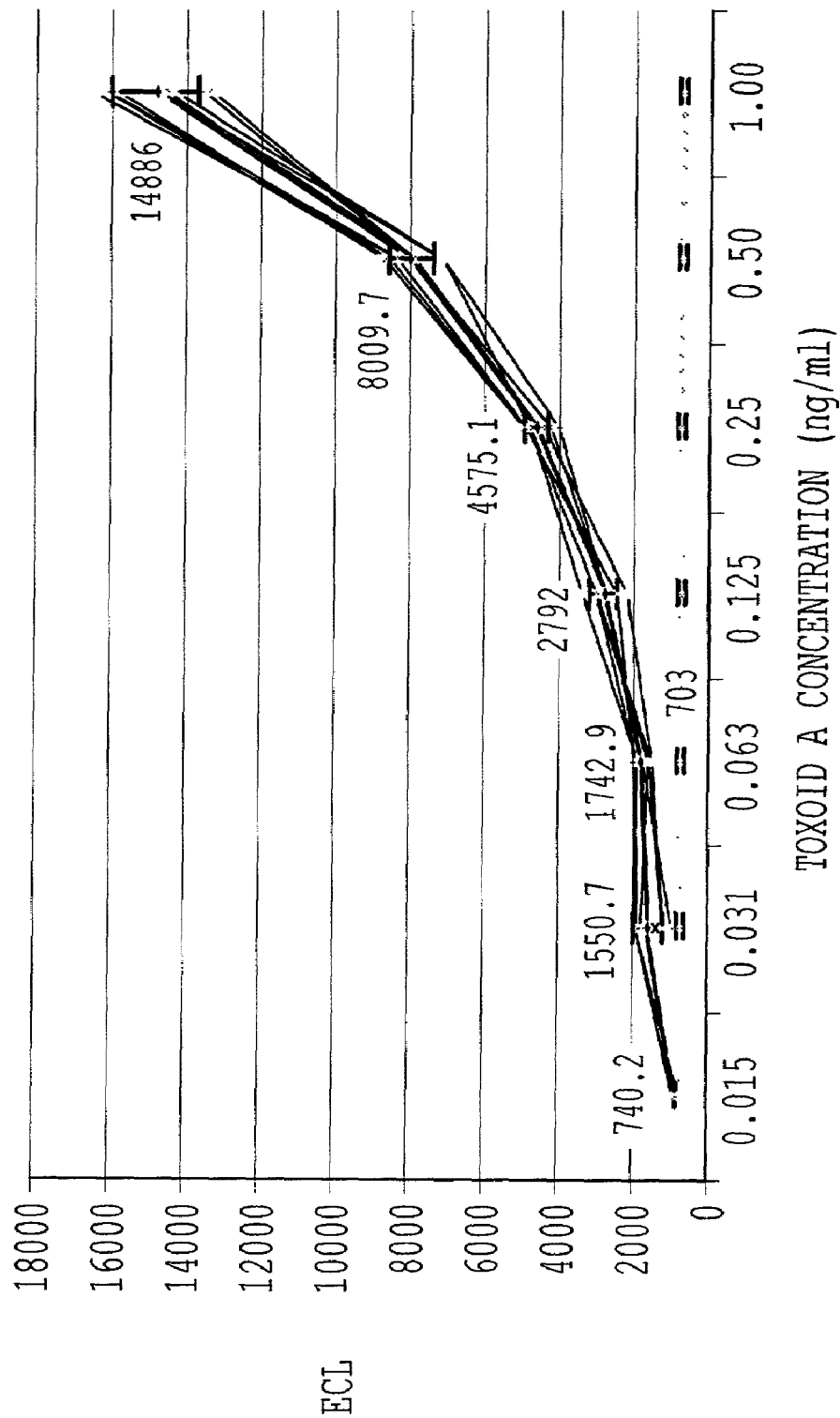
FIG. 10 is graph which shows the ECL units as a function of Toxoid A concentration (ng/ml) resulting from an experiment reported in the Examples.
Figure 11:
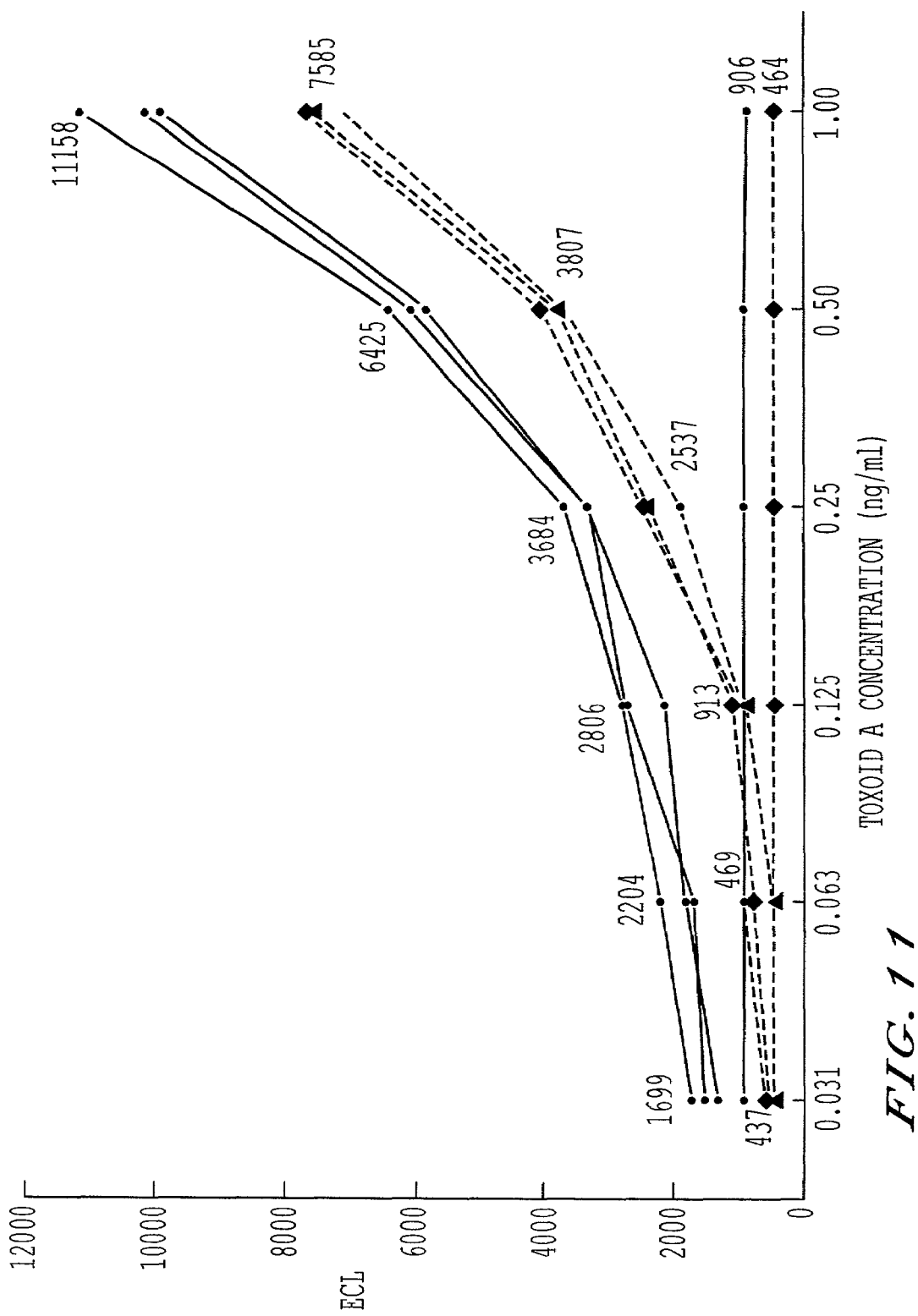
FIG. 11 is graph which shows the ECL units as a function of Toxoid A concentration (ng/ml) resulting from an experiment reported in the Examples.

Following freeze drying, each lyophilized product was evaluated using a 15-minute FASTube protocol. Background ECL traits and endpoint sensitivities were used to determine the effectiveness of the blocking constituents in FASTube assay formats for reduction of nonspecific adherence to the Dynabead. Fresh BG spore dilutions were prepared from $1\times10^7$ cfu/ml to $1\times10^1$ cfu/ml in 1× Threshold assay buffer. Table 7 shows the statistical analysis for the 0% block of Dynabead for this evaluation. The endpoint sensitivity is $1\times10^5$ cfu/ml of BG spores due to the high level nonspecific binding occurring in the assay. The data represent three replicate assays using the FASTube assay protocol for ECL measurement. Tables 8 to 11 display the statistical data analyses for BSA and Blotto, as well as a duplication of the goat serum evaluation from previous work. The tables show the comparative background reduction effected the various blocking constituents, as well as the assay endpoint sensitivities that were achieved by each prospective blocking agent. FIG. 6 describes the Signal to Noise Ratio for each constituent for BG detection. The data suggest that a 25% Blotto block is more effective in reducing background effects of nonspecific binding. The sensitivity cutoff was $1\times10^3$ cfu/ml BG spores compared to a cutoff of $1\times10^4$ cfu/ml for BSA and goat serum blocks. Background values for 25% Blotto blocks were approximately 3000 ECL, which was indicative of minimal conjugate adherence to the bead. Signal to Noise ratios also reflected the superiority of the Blotto block when compared to BSA or goat serum. Based upon the evaluations from this work, the follow on work focused on the determination of optimum percentages of Blotto block for the FASTube assay. Percentages of Blotto ranging from 0% to 25% were introduced into the study.

TABLE 7

Format A 0% Bead Block

| Sample ID | Mean | STD | % CV | S/N | +/−2STD |
|---|---|---|---|---|---|
| 0 | 171543 | 10652 | 6.21 | | 192848 |
| $10^3$ | 162850 | 10683 | 6.56 | 0.9 | |
| $10^4$ | 245019 | 9874 | 4.03 | 1.4 | |
| $10^5$ | 829570 | 39819 | 4.8 | 4.8 | |
| $10^6$ | 1483974 | 137416 | 9.26 | 8.7 | |

TABLE 8

Format A 5% BSA Block

| Sample ID | Mean | STD | % CV | S/N | +/−2STD |
|---|---|---|---|---|---|
| 0 | 57938 | 459.6 | 0.8 | 0 | 58857 |
| $10^3$ | 80488 | 3195 | 3.97 | 1.4 | |

TABLE 8-continued

Format A 5% BSA Block

| Sample ID | Mean | STD | % CV | S/N | +/−2STD |
|---|---|---|---|---|---|
| $10^4$ | 195806 | 28196 | 14.4 | 3.4 | |
| $10^5$ | 795907 | 33746 | 4.24 | 13.7 | |
| $10^6$ | 1465027 | 118667 | 8.1 | 25.3 | |

TABLE 9

Format A 25% Blotto Block

| Sample ID | Mean | STD | % CV | S/N | +/−2STD |
|---|---|---|---|---|---|
| 0 | 3521 | 408 | 11.6 | | 4337 |
| $10^3$ | 7057 | 688 | 9.75 | 2 | |
| $10^4$ | 29609 | 3120 | 10.54 | 8.4 | |
| $10^5$ | 171464 | 4183 | 2.44 | 48.7 | |
| $10^6$ | 351007 | 13435 | 3.8 | 99.7 | |

TABLE 10

Format A 25% Blotto Block

| Sample ID | Mean | STD | % CV | S/N | +/−2STD |
|---|---|---|---|---|---|
| 0 | 2925 | 448 | 15.33 | 0 | 3821 |
| $10^3$ | 6417 | 346 | 5.4 | 2.2 | |
| $10^4$ | 32068 | 1064 | 3.32 | 11 | |
| $10^5$ | 176375 | 2169 | 1.23 | 60.3 | |
| $10^6$ | 359453 | 17685 | 4.92 | 122.9 | |

TABLE 11

Format A 50% Goat Serum Block

| Sample ID | Mean | STD | % CV | S/N | +/−2STD |
|---|---|---|---|---|---|
| 0 | 32199 | 5461 | 16.96 | 0 | 43121 |
| $10^3$ | 38287 | 7181 | 19.54 | 1.2 | |
| $10^4$ | 72853 | 845 | 1.16 | 2.3 | |
| $10^5$ | 283957 | 9427 | 3.32 | 8.8 | |
| $10^6$ | 683814 | 66056 | 9.66 | 21.2 | |

Optimization of Percent Blotto Blocking Agent for FASTube Assay

Five 5-ml polypropylene Falcon tubes were labeled with series numbers 0% to 50%. To each tube, 450 μl of 1× lyophilization buffer was added, followed by the addition of 10.3 μl of biotin anti-BG IgG with gentle vortex. While vortexing, 110 μl of Dynabead M-280 were added sequentially to the tube and incubated for 15 minutes at ambient room temperature (approx. 26° C.). The bead-IgG complex was placed on a Nutator rotator for the incubation step to assure consistent suspension of the beads during incubation. At this point the volume per tube was 570.3 μl. After incubation, Blotto from 0% to 25% was added to respective tubes in the volumes indicated in Table 12. The Dynabead-IgG complex was incubated for 30 minutes at ART with gentle rocking on the rotator. Up to this point each blocking series was made simultaneously; however, ruthenium anti-BG conjugate was pipetted separately into the serum vials for lyophilization. The lower percent series were filled first; therefore, ruthenium anti-BG was absent from the blocking series at 20% and 25% for a longer period of time than for series at 5% or 10% (time interval was approximately 30 minutes). The standard lyophilization procedure was used for FASTube freeze drying. Table 13 shows the final volume additions of ruthenium anti-BG conjugate and 1× lyophilization buffer to each series. It is important to note that with the 1× lyophilization addition (1.6003 ml) to the blocked bead solution (1.140 ml), the final percentage of Blotto in the lyophilized product would be approximately 2.4 times less; i.e., 2.75 ml final volume divided by 1.140 ml block volume equals 2.4 (Table 13). This is significant because matrix effects might compromise ORIGEN® assays that exhibited a high concentration of Blotto in the final lyophilized product. However, in this case, with the reconstitution of the FASTube with 100 μl of sample and 200 μl of assay buffer, the overall Blotto percentage in ECL assays is described in Table 14. The final percentage of Blotto incorporation was calculated using a factor of "6" derived from 300 μl total volume for ECL assay divided by 50 μl of lyophilized product at "X" percent of Blotto.

TABLE 12

Amount of 50% Blotto Added to Dynabead-IgG Complex for Format A Blocking Step. Percent Block is based on Volume at 570.3 μl.

| Blotto Percent | Blotto Added (μl) | 1X Lyophilization Buffer (μl) | Final Incubation Volume (μl) |
|---|---|---|---|
| 0 | 0 | 570.32 | 1140.62 |
| 5 | 114.02 | 456.3 | 1140.62 |
| 10 | 228.08 | 342.2 | 1140.62 |
| 20 | 456.08 | 114.2 | 1140.62 |
| 25 | 570.3 | 0 | 1140.62 |

TABLE 13

Final Volume Additions of Ruthenium Anti-BG and 1X Lyophilization Buffer to Series

| Block Series % Blotto | Volume after Block (μl) | Ruthenium anti-BG (μl) | 1X Lyophilization Buffer (ml) | Final Volume (ml) |
|---|---|---|---|---|
| 0 | 1140.6 | 9.1 | 1.6003 | 2.75 |
| 5 | 1140.6 | 9.1 | 1.6003 | 2.75 |
| 10 | 1140.6 | 9.1 | 1.6003 | 2.75 |
| 20 | 1140.6 | 9.1 | 1.6003 | 2.75 |
| 25 | 1140.6 | 9.1 | 1.6003 | 2.75 |

TABLE 14

Final Percentage of Blotto in ECL FASTube Antigen Assays After Reconstitution with Aliquots of 50 μl of Sample.

| % Blotto Start Concentration | % Blotto for Bead Block (divide 2.4) | Lyophilization Volume (μl) | Reconstitution Volume (μl) | % Blotto in Final ECL Assay |
|---|---|---|---|---|
| 0 | 0 | 50 | 300 | 0 |
| 5 | 2.1 | 50 | 300 | 0.35 |
| 10 | 4.1 | 50 | 300 | 0.68 |
| 20 | 8.3 | 50 | 300 | 1.40 |
| 25 | 10.4 | 50 | 300 | 1.70 |

Results of 5% to 25% Blotto Block

Following freeze drying, each lyophilized product was evaluated using a 15-minute FASTube protocol. Background ECL units and endpoint sensitivities were used to determine the effectiveness of the blocking constituents for reduction of nonspecific adherence to the Dynabead. Fresh BG spore dilutions were prepared from $1\times10^7$ cfu/ml to $1\times10^1$ cfu/ml in 1× Threshold assay buffer. Tables 15 to 18 present the statistical analysis for the percent block of Dynabead for this evaluation. The endpoint sensitivity was $1\times10^3$ cfu/ml of BG spores for all Blotto percentage incorporations. The data represent three replicate assays using the FASTube assay protocol for ECL measurement. FIG. 7 shows the relationship of the Blotto block percentages from 5% to 25% in Signal to Noise ratio. The data indicate that higher percentage Blotto blocks (20 to 25%) appear to significantly reduce the background effects caused by nonspecific binding of ruthenium antibody conjugate to the bead by 20-fold. The background for a 0% block was approximately 84,000 ECL compared to a background of 3000 to 4000 ECL for 25% Blotto blocks. The data also suggest that there were no matrix effects for the ECL assay at the higher Blotto percentages.

TABLE 15

Format A 5% Blotto

| Sample ID | Mean | STD | % CV | S/N | +/−2STD |
|---|---|---|---|---|---|
| 0 | 16070 | 2367 | 14.73 | 0 | 20804 |
| $10^3$ | 20174 | 2324 | 11.52 | 1.3 | |
| $10^4$ | 77085 | 13459 | 17.46 | 4.8 | |
| $10^5$ | 364858 | 226577 | 6.21 | 22.7 | |
| $10^6$ | 697211 | 56055.8 | 8.04 | 43.4 | |

TABLE 16

Format A 10% Blotto

| Sample ID | Mean | STD | % CV | S/N | +/−2STD |
|---|---|---|---|---|---|
| 0 | 7376 | 109 | 1.48 | | +8094 |
| $10^3$ | 12896 | 261 | 2.03 | 1.75 | |
| $10^4$ | 52123 | 891 | 1.71 | 7.1 | |
| $10^5$ | 209266 | 9605 | 4.59 | 39.4 | |
| $10^6$ | 516024 | 27968 | 5.42 | 70 | |

TABLE 17

Format A 20% Blotto

| Sample ID | Mean | STD | % CV | S/N | +/−2STD |
|---|---|---|---|---|---|
| 0 | 5568 | 1182 | 21.24 | | +7933 |
| $10^3$ | 9764 | 426 | 4.37 | 1.8 | −8910 |
| $10^4$ | 4273 | 168 | 3.95 | 8 | |
| $10^5$ | 251211 | 10349 | 4.12 | 45.1 | |
| $10^6$ | 440598 | 39874 | 9.05 | 79.1 | |

TABLE 18

Format A 25% Blotto

| Sample ID | Mean | STD | % CV | S/N | +/−2STD |
|---|---|---|---|---|---|
| 0 | 4214 | 214 | 5.08 | | +4642 |
| $10^3$ | 8359 | 1008 | 12.06 | 2 | −6343 |
| $10^4$ | 36135 | 661 | 1.83 | 8.6 | |
| $10^5$ | 198718 | 17129 | 8.62 | 47.2 | |
| $10^6$ | 386883 | 4333 | 1.12 | 91.8 | |

Format B Bead Blocking Procedure with Blotto and Goat IgG

A second blocking format was designed for additional evaluation of assay background responses. In Format B, the advantage of pre-blocking the bead with either goat IgG or Blotto before immobilization of the capture antibody was examined. A blocking step was designed to incorporate Blotto and goat IgG (Sigma Cat. I-5256, lot #055H8855) into the procedure at series 0%, 2.5%, 5%, 10%, 15%, and 25% for Blotto (stock @ 50%) and 0%, 5%, 10%, 20% 30%, and 50% for goat IgG. Dynabead M-280 Streptavidin (IGEN Cat. #402-175-01, lot #7030) at 10 mg/ml was blocked separately during the process. A total of 24 tests were prepared for each blocking series. This would provide data for one run per 8 dilutions of BG spores for each series. Once the reagents were prepared, six 1.8-ml polypropylene microfuge tubes for each blocking agent were labeled with series numbers 0% to 25% for goat IgG and Blotto samples. To each tube, 60 µl of Dynabead M-280 was added, followed by the addition of either Blotto or goat IgG with gentle rocking for 45 minutes on a Nutator rotator for the incubation step to assure consistent suspension of the beads during incubation. The volume per tube is listed in Table 19 describing amounts of blocking agent added to respective tubes. After vortexing, each microfuge tube was placed into a Dynal Microparticle Concentrator (Dynal WPC-E Cat. 3 120.04) for 3 minutes, followed by aspiration of the liquid. The beads were washed by placing 145 µl of 0.01 M PBS to each tube, followed by a gentle vortex per tube. Each tube was placed in the MPC for 3 minutes to immobilize the beads for aspiration of the supernatant. Each tube received 40 µl of 1× lyophilization buffer for final volume adjustment. The bead-buffer solution was suspended by vortexing, followed by the addition of 6 µl of biotinylated antibody conjugate. The Dynabead-IgG complex was incubated for 15 minutes at ART with gentle rocking on the rotator. The 15-minute incubation period was selected arbitrarily and was not based on any previous experience with this particular blocking format; however, if the block proved to be inefficient, future efforts would utilize longer blocking periods and/or blocking at 37° C. Each tube received 1.449 ml of 1× lyophilization buffer to a volume of 1.495 ml. Ruthenium anti-BG conjugate (5 µl) was added separately as each series was prepared for lyophilization. The standard lyophilization procedure was used. Table 20 shows the final volume additions of ruthenium anti-BG conjugate and 1× lyophilization buffer to each series.

TABLE 19

Amount of Blocking Agent Added to Dynabeads for Format B Blocking Step. Percent Block is Based on Volume of Dynabeads at 60 µl.

| Block Series % Goat IgG | Goat IgG (µl) | Block Series % Blotto | Blotto (µl) (50% stock) |
|---|---|---|---|
| 0 | 0 | 0 | 0 |
| 5 | 3 | 2.5 | 5 |
| 10 | 6 | 5 | 10 |
| 20 | 12 | 10 | 20 |
| 30 | 18 | 15 | 30 |
| 50 | 30 | 25 | 50 |

TABLE 20

Final Volume Additions

| Block Series | Volume after Block | Ruthenium anti-BG | 1X Lyophilization Buffer | Final Volume |
|---|---|---|---|---|
| 0 | 40 µl | 5 µl | 1.449 ml | 1.50 ml |

Results of Format B Goat IgG and Blotto Block

Following freeze drying, each lyophilized product was evaluated using a 15-minute FASTube protocol. Background ECL units and endpoint sensitivities were used to determine the effectiveness of using the blocking constituents for reduction of nonspecific adherence to the Dynabead. Fresh BG spore dilutions were prepared from $1 \times 10^7$ cfu/ml to $1 \times 10^1$ cfu/ml in 1× Threshold assay buffer. Tables 21 and 22 present the results of blocking effectiveness using Format B for Blotto and goat IgG. The endpoint sensitivity was $1 \times 10^4$ cfu/ml of BG spores for all Blotto percentage incorporations and $10^5$ cfu/ml for goat IgG. The data represent three replicate assays using the FASTube assay protocol for ECL measurement. The data suggest that a Dynabead pre-block was not as effective in reducing FASTube assay background as Format A blocking measures. Format B goat IgG block was the least effective blocking agent. Format B Blotto block provided significant reduction of nonspecific binding (up to 70% effective); however, background values for Format A Blotto blocks were 17-fold lower than for Format B. A magnitude of detection was sacrificed using Format B blocking procedure. One reason may be that the PBS wash of immobilized bead after the blocking step may remove all blocking agent activity; whereas, in Format A the blocking agent is not removed or washed, but diluted by 1× lyophilization buffer before pipetting into the serum vials. Perhaps the wash step for Format B is unnecessary and could be eliminated.

TABLE 21

Format B FASTube Results for Blotto Block.

| % Block | ECL value | Difference | % Decrease | Sensitivity |
|---|---|---|---|---|
| 0% | 233299 | | | $10^5$ at 3.5 |
| 2.5% | 111541 | 121758 | 52.2 | $10^4$ at 2.4 |
| 5% | 110324 | 122873 | 52.7 | $10^4$ at 2.2 |
| 10% | 86426 | 146873 | 63 | $10^4$ at 3.0 |
| 15% | 102822 | 130477 | 56 | $10^4$ at 2.5 |
| 25% | 69540 | 163759 | 70 | $10^4$ at 3.7 |

TABLE 22

Format B FASTube Results for Goat IgG Block.

| % Block | ECL value | Difference | % Decrease | Sensitivity |
|---|---|---|---|---|
| 0% | 233299 | | | $10^5$ at 3.5 |
| 5% | 191376 | 41923 | 18 | $10^5$ at 3.4 |
| 10% | 138393 | 94906 | 41 | $10^5$ at 4.4 |
| 20% | 150000 | 83299 | 36 | $10^5$ at 3.5 |
| 30% | 183166 | 50133 | 21.5 | $10^5$ at 3.5 |
| 50% | 153297 | 80002 | 34.3 | $10^5$ at 4.1 |

Final Analysis of Blocking Formats for FASTube Assay

The immunomagnetic particles were blocked using two formats. Format A relied upon the immobilization of available biotinylated anti-BG IgG prior to the addition of blocking agents at various percentages (v/v) in the complex. Format B proceeded with a Dynabead pre-block of blocking agents in various percentages, followed by a wash step and eventual immobilization of anti-BG conjugate to the streptavidin moieties on the bead. Based upon the data derived from blocking experiments using Blotto, goat serum, and goat IgG at percentages from 0% to 50%, Format A (beginning with a 25% Blotto suspension and 10.4% Dynabead block incorporation) provided the most effective blocking of polystyrene sites on the bead. A 20-fold reduction in background effects was observed. Therefore, Format A will be used for the present effort for ECL FASTube assays. A 50% Blotto suspension will be used to provide a 10.4% Dynabead bead block. As discussed earlier, Format B may be more effective if the wash step after blocking is eliminated. Also, many other blocking agents that are commercially available could be utilized effectively in this procedure.

FASTube Assay with Additional Biologicals

Two additional assays that were significant to the medical, environmental, and food safety domain were studied. One toxin assay, Clostridium botulinum A neurotoxin (BoTx), and a bacterial vegetative cell, Escherichia coli 0157, were selected for this work. In addition, the BG FASTube assay was duplicated during the course of this effort. The preparation of goat anti-BoTx biotin and goat anti-BoTx ruthenium conjugates; goat anti-E. coli 0157 biotin and goat anti-E. coli 0157 ruthenium conjugates; and, of goat anti-BG biotin and goat anti-BG ruthenium conjugates was performed in a manner consistent with standard protocols used for labeling IgG for ORIGEN® use. The resulting MIRs of goat anti-BoTx biotin were 2.4 at 0.25 mg/ml and goat anti-BoTx ruthenium was 7.6 at a concentration of 0.17 mg/ml. The MIRs of goat anti-E. coli biotin were 3.5 at 0.28 mg/ml and goat anti-E. coli ruthenium was 10.3 at a concentration of 0.22 mg/ml. The MIRs of goat anti-BG biotin were 4.0 at 0.18 mg/ml and goat anti-BG ruthenium was 8.5 at a concentration of 0.25 mg/ml. The total number of tests to be prepared for each antibody series was 500 in the case of C. botulinum A neurotoxin and E. coli. and 1140 for BG. All three FASTube antigen assays were prepared using a 50% Blotto suspension with incorporation of a 10.4% Dynabead bead pre-block before lyophilization. The following protocol was used for C. botulinum A neurotoxin and Escherichia coli (E. coli) FASTube antigen assay development.

Immunobilization of Biotinylated Antibody Conjugates to Dynabead M-280 Streptavidin Two 50-ml polypropylene sterile Falcon tubes were labeled with BoTx FASTube and E. coli FASTube, respectively. The appropriate volume of 1× lyophilization buffer was placed in each of the two labeled Falcon tubes, followed by the addition of the specified volumes of biotin anti-XXX for each FASTube assay (see Table 23). One ml of Dynabead M-280 streptavidin (Cat #402-175-01, lot #7119) were added sequentially to each tube, and the tube was incubated for 1 hour at ambient room temperature (ART, approx. 26° C.). The bead-IgG complex was placed on a Nutator rotator for the incubation step to assure consistent suspension of the beads during incubation. At this point the volume per tube was 5 ml. The Dynabead IgG complex was incubated for 1 hour at ART with gentle rocking on the rotator. The 1 hour incubation period was selected arbitrarily and was not based on any previous experience with this particular blocking format; however, if the block proved to be inefficient, future efforts would utilize longer blocking periods and/or blocking at 37° C.

TABLE 23

Sequential Addition of FASTube BoTx and E. coli Biotin Conjugate and Dynabead M-280. Reagents prior to Bead Block.

| Sequential Addition | BoTx FASTube | E. coli FASTube |
|---|---|---|
| 1X Lyophilization Buffer | 3.900 ml | 3.908 ml |
| Biotinylated Antibody | 0.100 ml | 0.0089 ml |
| Dynabead M-280 | 1.000 ml | 1.000 ml |
| Total volume | 5.000 ml | 5.000 ml |

Blotto Block of Dynabead M-280 Streptavidin

A 50% Blotto suspension was prepared for the blocking step. Three ml of 1× lyophilization buffer was added to each FASTube for a total volume of 8.000 ml. To achieve a 10% Blotto block (v/v), 2 ml of 50% Blotto was added to each tube slowly with gentle vortex action. The bead/Blotto complex was incubated for 2 hours at ART on a Clay Adams Nutator. Subsequent to the bead block, a specified amount of ruthenium conjugate was added to the BoTx and E. coli FASTube respectively. Table 24 shows the final volume additions of ruthenium anti-BoTx and ruthenium anti-E. coli conjugate and 1× lyophilization buffer to each series.

TABLE 24

Final Volume Additions of Ruthenium Anti-BoTx and Ruthenium Anti-E. coli and 1X Lyophilization Buffer to Preparation

| Final Addition | BoTx FASTube | E. coli FASTube |
|---|---|---|
| Blotto Block Volume | 10.000 ml | 10.000 ml |
| 1X Lyophilization Buffer | 14.853 ml | 14.886 ml |
| Ruthenium Conjugate | 0.147 ml | 0.114 ml |
| Total volume | 25.000 ml | 25.000 ml |

Lyophilization of BoTx and E. coli FASTube

The lyophilization protocol was used to freeze dry the BoTx and E. coli FASTube assays. Two lyophilization shelves were lined each with 480 lyophilization vials. BoTx FASTube tests were placed in the top shelf A, and E. coli FASTube tests were placed in the bottom shelf B. Using an Eppendorf Repeater Pipetter and sterile 2.5 ml Combitip (Cat. #22-26-120-7), each lyophilization vial (West Company Cat. #6800-0313) received 50 µl of the appropriate FASTube reagent. Subsequently a 13 mm gray butyl stopper (West Company Cat. #1012-3516) was placed on each vial. The lyophilization run was carried out overnight, and after the lyophilization run was completed, the vials were sealed under vacuum (75 mT) and removed from the freeze drier. The vials were immediately sealed for long-term storage with 13 mm flip-tear off aluminum crimp seals. The FASTube assays were then evaluated on the ECL Analyzer.

Immobilization of Biotinylated Antibody Conjugates to Dynabead M-280 Streptavidin One 50 ml polypropylene sterile Falcon tube was labeled as BG FASTube. The biotinylated antibody conjugate was added to 10.81 ml of 1× lyophilization buffer in the Falcon tube. 2.8 ml of Dynabead M-280 streptavidin was added sequentially to the tube, and the tube was incubated for 1 hour at ambient room temperature (ART, approx. 26° C.). The bead-IgG complex was placed on a Nutator rotator for the incubation step to assure consistent suspension of the beads during incubation. At this point the volume was 14 ml. The Dynabead-IgG complex was incubated for 1 hour at ART with gentle rocking on the rotator.

Blotto Block of Dynabead M-280 Streptavidin

A 50% Blotto suspension was prepared for the blocking step. The addition of 8.400 ml of 1× lyophilization buffer was added to the bead-IgG complex (14.000 ml) from the previous immobilization step for a volume of 18.400 ml. To achieve a 10% Blotto block (v/v), 5.600 ml of 50% Blotto was added to the tube slowly with gentle vortex action (28.000 ml total volume). The bead/Blotto complex was incubated for 2 hours at ART on a Clay Adams Nutator. Subsequent to the bead block, a specified amount of ruthenium conjugate was added to the BG FAST tube respectively. Table 26 shows the final volume additions of ruthenium anti-BG conjugate and 1× lyophilization buffer.

TABLE 25

Sequential Addition of FASTube BG Biotin Conjugate and Dynabead M-280 Reagents prior to Bead Blocks.

| Sequential Addition | BG FASTube |
| --- | --- |
| 1X Lyophilization Buffer | 10.810 ml |
| Biotinylated Antibody | 0.389 ml |
| Dynabead M-280 | 2.800 ml |
| Total volume | 14.000 ml |

TABLE 26

Final Volume Additions of Ruthenium Anti-BG and 1X Lyophilization Buffer to Preparation.

| Final Additions | BG FASTube |
| --- | --- |
| Blotto Block Volume | 28.000 ml |
| 1X Lyophilization Buffer | 41.720 ml |
| Ruthenium Conjugate | 0.280 ml |
| Total volume | 70.000 ml |

Lyophilization of BG FASTube

The lyophilization protocol found on page 7 of this disclosure was used to freeze dry the BG FASTube assays. Two lyophilization shelves were lined each with 570 lyophilization vials. Using an Eppendorf Repeater Pipetter and sterile 2.5 ml Combitip, each lyophilization vial (West Company Cat. #6800-0313) received 50 µl of the appropriate FASTube reagent. Subsequently a 13 mm gray butyl stopper (West Company Cat. #1012-3516) was placed on each vial. The lyophilization run was carried out over two nights, and after the lyophilization run was completed, the vials were sealed under vacuum (75 mT) and removed from the freeze drier. The vials were immediately sealed for long term storage with 13 mm flip-tear off aluminum crimp seals. The FASTube assays were then evaluated on the ECL Analyzer.

FASTube Results

Commercially purchased solid food samples for *C. botulinum* A toxoid were prepared in accordance with the *USDA/FSIS Microbiology Laboratory Guidebook*, 3$^{rd}$ ed. Chapter 14: "Methods for the Detection of *C. Botulinum* Toxins in Meat and Poultry Products," 1998, which is incorporated herein by reference. Twenty-five (25) grams of solid food sample was homogenized in 50 ml 0.2M sodium phosphate buffer, pH 7.7. The homogenate was clarified by centrifugation at 15,000×g for 15 min at 5° C. The supernatant was diluted 1:10 with buffer and sterile filtered for subsequent toxoid spikes. Liquid samples were diluted 1:2 with buffer and sterile filtered prior to spiking. An addition of 0.1% BSA and 0.025% Triton X-100(v/v) was added to each prep before filtering to eliminate nonspecific binding of toxoid. Botulinum A toxoid (Wako Pure Chemicals Industries, Ltd., Japan, #005-76000, WDG 7187) was spiked at concentrations of (ng/ml) 0.015, 0.031, 0.063, 0.125, 0.25, 0.50, 1, 5, 10, and 25 into food and liquid samples. Heat killed *Escherichia coli* 0157 cells (Kirkegaard & Perry Laboratories, Inc., KPL, #50-95-90) were serially diluted from $1 \times 10^9$ cfu/ml to $1 \times 10^1$ cfu/ml for evaluation.

Results of BoTx FASTube Antigen Assays

A total of 296 Botulinum A FASTube assays were evaluated in 5 sample milieus. Detection of spiked toxoid in the low picogram (pg) range was possible for all samples with endpoint sensitivities of 63 to 125 pg/ml for all assays with a dynamic range of seven toxoid dilutions. There occurred one false positive response and one false negative response for 296 assays. The percent error was <0.1%. FIGS. 8 to 11 describe the sensitivity and detection for the BoTx FASTube assay.

Results of *Escherichia coli* 0157 FASTube Assays

The *E. coli* FASTube assay in pristine laboratory buffer samples demonstrated an endpoint sensitivity of $10^2$ cfu/ml. The probability that *E. coli* soluble antigens contributed to the low endpoint sensitivity measurement at low titrations is a reasonable conclusion. In any case, the *E. coli* ECL FASTube assay was shown to be a feasible format for detection of the bacteria in clinical or food samples. Additional assays are planned in various sample milieus such as, ground meats, seafood, and juices. The low ECL background demonstrates the effectiveness of the Dynabead pre-block with Blotto before the addition of the ruthenium antibody to the lyophilization mixture. Previous work has shown the mean ECL background value for a non-blocked assay to be 22,319 (n=6). Therefore, the pre-block with Blotto reduces the ECL background four-fold and permits the lyophilization of all assay components into one tube. Since the reporter antibody is not adhering nonspecifically to the bead, the opportunity for optimal formation of the ECL immunocomplex contributes to the sensitivity of the overall assay. Table 27 describes the endpoint sensitivity for the ECL *E. coli* FASTube Assay.

TABLE 27

*E. coli* FASTube Assay spiked at 0 to $10^4$ cfu/ml in pristine laboratory buffer milieu. DGM log #98-0008-133, Feb. 4, 1999

| *E. coli* Concentration cfu/ml | No. of Replicates | ECL | S/N Ratio |
| --- | --- | --- | --- |
| Background | 10 | 5909 | 1.0 |
| $10^2$ | 6 | 9466.5 | 1.6 |
| $10^3$ | 6 | 37,229 | 6.3 |
| $10^4$ | 6 | 190,159 | 32.2 |

Results FASTube Antigen Assays Lot #98-0008-88

The ECL BG FASTube assay which had been developed as the model assay was repeated to ascertain the reproducibility of the overall procedures involved in the Dynabead pre-block with 10.4% Blotto and subsequent lyophilization. Efforts were made to maintain consistency in the preparation of the reagents as well as provide uniformity in the process. Subsequent to lyphoilization, nine replicate data points were generated for assessment of ECL background effects. The endpoint sensitivity for the assay was $1\times10^3$ cfu/ml with mean ECL background values at 5193. Table 28 describes the endpoint sensitivity for the ECL BG FASTube assay. Table 29 describes the endpoint sensitivity for the ECL BG FASTube assay developed as the model assay. A comparison of the ECL background and titration data demonstrate the reproducibility of the procedure.

TABLE 28

BG FASTube Assay spiked at 0 to $10^4$ cfu/ml in pristine laboratory buffer sample milieu.

| BG Concentration (cfu/ml) | No. of Replicates | ECL | S/N Ratio |
|---|---|---|---|
| Background | 9 | 5193 | 1.0 |
| $10^3$ | 3 | 9641 | 1.85 |
| $10^4$ | 3 | 53,212 | 10.2 |
| $10^5$ | 3 | 384,045 | 74 |

TABLE 29

BG FASTube Model Assay spiked at 0 to $10^4$ cfu/ml in pristine laboratory buffer sample milieu.

| Sample ID (n = 3) | Mean | STD | % CV | S/N | +/−2STD |
|---|---|---|---|---|---|
| 0 | 7376 | 109 | 1.48 | | +8094 |
| $10^3$ | 12896 | 261 | 2.03 | 1.75 | |
| $10^4$ | 52123 | 891 | 1.71 | 7.1 | |
| $10^5$ | 209266 | 9605 | 4.59 | 39.4 | |
| $10^6$ | 516024 | 27968 | 5.42 | 70 | |

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What is claimed is:

1. A kit, comprising:
    (A) a container; and
    (B) a reagent mixture comprising:
        (1) an immobilized capture antibody; and
        (2) a labeled reporter antibody,
    wherein said immobilized capture antibody and said labeled reporter antibody bind specifically to a same analyte, and wherein said reagent mixture has been prepared by drying a liquid comprising said labeled reporter antibody in the presence of said immobilized capture antibody, and wherein said reagent mixture is contained in said container, and
        wherein said container is a tube that is hermetically sealed and wherein said tube comprises an indentation near the open end.
2. The kit of claim 1, wherein said capture antibody is immobilized on a paramagnetic bead.
3. The kit of claim 1, wherein said drying is carried out by lyophilization.
4. The kit of claim 1, wherein said labeled reporter antibody is labeled with a tris bipyridyl ruthenium group.
5. The kit of claim 1, wherein said tube has dimensions of about 12 mm×about 75 mm.
6. The kit of claim 1, wherein said tube is a polypropylene tube.
7. The kit of claim 1, wherein said immobilized capture antibody is specific for a *Clostridium botulinum* A neurotoxin antigen.
8. The kit of claim 1, wherein said immobilized capture antibody is specific for a bacterial toxin, a virus, a bacteria, a protein, a hormone, a DNA, a RNA, a drug, an antibiotic, or a nerve toxin.
9. The kit of claim 1, wherein said immobilized capture antibody is specific for a bacterial toxin, a virus, a bacteria, or a nerve toxin.
10. A method for detecting or quantifying an analyte, comprising:
    (i) providing a kit comprising:
        (A) a container, and
        (B) a reagent mixture comprising:
            (1) an immobilized capture antibody; and
            (2) a labeled reporter antibody,
        wherein said immobilized capture antibody and said labeled reporter antibody bind specifically to a same analyte, and wherein said reagent mixture has been prepared by drying a liquid comprising said labeled reporter antibody in the presence of said immobilized capture antibody, and wherein said reagent mixture is contained in said container, and
            wherein said container is a tube that is hermetically sealed and wherein said tube comprises an indentation near the open end;
    (ii) incubating a liquid sample, which may contain said analyte, with said reagent mixture;
    (iii) measuring a signal attributable to a complex formed by binding of said immobilized capture antibody and said labeled reporter antibody to said analyte; and
    (iv) correlating said measured signal to the presence or amount of said analyte.
11. The method of claim 10, wherein said capture antibody is immobilized on a paramagnetic bead.
12. The method of claim 10, wherein said drying is carried out by lyophilization.
13. The method of claim 10, wherein said signal is an electrochemiluminescent signal.
14. The method of claim 10, wherein said labeled reporter antibody is labeled with a tris bipyridyl ruthenium group.
15. The method of claim 10, wherein said tube has dimensions of about 12 mm×about 75 mm.
16. The method of claim 10, wherein said tube is a polypropylene tube.
17. The method of claim 10, wherein said immobilized capture antibody is specific for a *Clostridium botulinum* A neurotoxin antigen.
18. The method of claim 10, wherein said immobilized capture antibody is specific for a bacterial toxin, a virus, a bacteria, a protein, a hormone, a DNA, a RNA, a drug, an antibiotic, or a nerve toxin.
19. The method of claim 10, wherein said immobilized capture antibody is specific for a bacterial toxin, a virus, a bacteria, or a nerve toxin.
20. A reagent mixture, comprising:
    (1) an immobilized capture antibody; and
    (2) a labeled reporter antibody,
wherein said immobilized capture antibody and said labeled reporter antibody bind specifically to a same analyte, and wherein said reagent mixture has been prepared by drying a mixture of (a) a liquid comprising said labeled reporter antibody and (b) said immobilized capture antibody,
    wherein said reagent mixture is contained in a tube that is hermetically sealed and wherein said tube comprises an indentation near the open end.

21. The reagent mixture of claim 20, wherein said reagent mixture is prepared by a process which comprises:
(1) forming a liquid which comprises said labeled reporter antibody;
(2) adding said liquid which comprises said labeled reporter antibody to said tube, wherein said capture antibody is contained in said tube; and
(3) drying said liquid which comprises said labeled reporter antibody, to obtain said reagent mixture.

22. The reagent mixture of claim 21, wherein said drying is lyophilizing.

23. The reagent mixture of claim 20, wherein said liquid is an aqueous solution.

24. The reagent mixture of claim 20, wherein said reagent mixture is an intimate mixture of said labeled reported antibody and said immobilized capture antibody.

25. The reagent mixture of claim 20, wherein said tube has dimens ions of about 12 mm×about 75 mm.

26. The reagent mixture of claim 20, wherein said tube is a polypropylene tube.

27. The reagent mixture of claim 20, wherein said immobilized capture antibody is specific for a *Clostridium botulinum* A neurotoxin antigen.

28. The reagent mixture of claim 20, wherein said immobilized capture antibody is specific for a bacterial toxin, a virus, a bacteria, a protein, a hormone, a DNA, a RNA, a drug, an antibiotic, or a nerve toxin.

29. The reagent mixture of claim 20, wherein said immobilized capture antibody is specific for a bacterial toxin, a virus, a bacteria, or a nerve toxin.

30. A kit, comprising:
(A) a container; and
(B) a reagent mixture comprising:
(1) an immobilized capture antibody; and
(2) a labeled reporter antibody,
wherein said immobilized capture antibody and said labeled reporter antibody bind specifically to a same analyte, and wherein said reagent mixture has been prepared by drying a liquid comprising said labeled reporter antibody in the presence of said immobilized capture antibody, and wherein said reagent mixture is contained in a hermetically sealed tube.

31. The kit of claim 30, wherein said capture antibody is immobilized on a paramagnetic bead.

32. The kit of claim 30, wherein said drying is carried out by lyophilization.

33. The kit of claim 30, wherein said labeled reporter antibody is labeled with a tris bipyridyl ruthenium group.

34. The kit of claim 30, wherein said tube has dimensions of about 12 mm×about 75 mm.

35. The kit of claim 30, wherein said tube is a polypropylene tube.

36. The kit of claim 30, wherein said immobilized capture antibody is specific for a *Clostridium botulinum* A neurotoxin antigen.

37. The kit of claim 30, wherein said immobilized capture antibody is specific for a bacterial toxin, a virus, a bacteria, a protein, a hormone, a DNA, a RNA, a drug, an antibiotic, or a nerve toxin.

38. The kit of claim 30, wherein said immobilized capture antibody is specific for a bacterial toxin, a virus, a bacteria, or a nerve toxin.

39. A method for detecting or quantifying an analyte, comprising:
(i) providing a kit comprising:
(A) a container, and
(B) a reagent mixture comprising:
(1) an immobilized capture antibody; and
(2) a labeled reporter antibody,
wherein said immobilized capture antibody and said labeled reporter antibody bind specifically to a same analyte; and wherein said reagent mixture has been prepared by drying a liquid comprising said labeled reporter antibody in the presence of said immobilized capture antibody, and wherein said reagent mixture is contained in a hermetically sealed tube;
(ii) incubating a liquid sample, which may contain said analyte, with said reagent mixture;
(iii) measuring a signal attributable to a complex formed by binding of said immobilized capture antibody and said labeled reporter antibody to said analyte; and
(iv) correlating said measured signal to the presence or amount of said analyte.

40. The method of claim 39, wherein said capture antibody is immobilized on a paranlagnetic bead.

41. The method of claim 39, wherein said drying is carried out by lyophilization.

42. The method of claim 39, wherein said signal is an electrochemiluminescent signal.

43. The method of claim 39, wherein said labeled reporter antibody is labeled with a tris bipyridyl ruthenium group.

44. The method of claim 39, wherein said tube has dimensions of about 12 mm×about 75 mm.

45. The method of claim 39, wherein said tube is a polypropylene tube.

46. The method of claim 39, wherein said immobilized capture antibody is specific for a *Clostridium botulinum* A neurotoxin antigen.

47. The method of claim 39, wherein said immobilized capture antibody is specific for a bacterial toxin, a virus, a bacteria, a protein, a hormone, a DNA, a RNA, a drug, an antibiotic, or a nerve toxin.

48. The method of claim 39, wherein said immobilized capture antibody is specific for a bacterial toxin, a virus, a bacteria, or a nerve toxin.

49. A reagent mixture, comprising:
(1) an immobilized capture antibody; and
(2) a labeled reporter antibody,
wherein said immobilized capture antibody and said labeled reporter antibody bind specifically to a same analyte, and wherein said reagent mixture has been prepared by drying a mixture of (a) a liquid comprising said labeled reporter antibody and (b) said immobilized capture antibody,
wherein said reagent mixture is contained in a hermetically sealed tube.

50. The reagent mixture of claim 49, wherein said reagent mixture is prepared by a process which comprises:
(1) forming a liquid which comprises said labeled reporter antibody;
(2) adding said liquid which comprises said labeled reporter antibody to said tube, wherein said capture antibody is contained in said tube; and
(3) drying said liquid which comprises said labeled reporter antibody, to obtain said reagent mixture.

51. The reagent mixture of claim 50, wherein said drying is lyophilizing.

52. The reagent mixture of claim 51, wherein said liquid is an aqueous solution.

53. The reagent mixture of claim 49, wherein said reagent mixture is an intimate mixture of said labeled reported antibody and said immobilized capture antibody.

54. The reagent mixture of claim 49, wherein said tube has dimensions of about 12 mm×about 75 mm.

55. The reagent mixture of claim 49, wherein said tube is a polypropylene tube.

56. The reagent mixture of claim 49, wherein said immobilized capture antibody is specific for a *Clostridium botulinum* A neurotoxin antigen.

57. The reagent mixture of claim 49, wherein said immobilized capture antibody is specific for a bacterial toxin, a virus, a bacteria, a protein, a hormone, a DNA, a RNA, a drug, an antibiotic, or a nerve toxin.

58. The reagent mixture of claim 49, wherein said immobilized capture antibody is specific for a bacterial toxin, a virus, a bacteria, or a nerve toxin.

* * * * *

UNITED STATES PATENT AND TRADEMARK OFFICE
CERTIFICATE OF CORRECTION

PATENT NO. : 7,141,436 B2  
APPLICATION NO. : 10/147965  
DATED : November 28, 2006  
INVENTOR(S) : Deborah L. Gatto-Menking et al.

Page 1 of 1

It is certified that error appears in the above-identified patent and that said Letters Patent is hereby corrected as shown below:

Column 5, line 31, " and Balckburn, G.F., et al, "
  should read -- and Blackburn, G.F., et al. --.

Column 32, line 17, " immobilized on a paranlagnetic bead. "
  should read -- immobilized on a paramagnetic bead. --.

Signed and Sealed this

Eleventh Day of December, 2007

JON W. DUDAS  
*Director of the United States Patent and Trademark Office*